United States Patent
Mirzabekov et al.

(10) Patent No.: US 6,440,671 B1
(45) Date of Patent: *Aug. 27, 2002

(54) USE OF CONTINUOUS/CONTIGUOUS STACKING HYBRIDIZATION AS A DIAGNOSTIC TOOL

(75) Inventors: Andrei Darievich Mirzabekov; Eugene Vladislavovich Kirillov; Sergei Valeryevich Parinov; Victor Evgenievich Barski, all of Moscow; Svetlana Alekseevna Dubiley, Kiev, all of (RU)

(73) Assignee: The University of Chicago, Chicago, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 09/498,851

(22) Filed: Feb. 7, 2000

Related U.S. Application Data

(60) Division of application No. 08/855,372, filed on May 13, 1997, now Pat. No. 6,090,549, which is a continuation-in-part of application No. 08/587,332, filed on Jan. 16, 1996, now Pat. No. 5,908,745.

(51) Int. Cl.⁷ ............................ C12Q 1/68; C12P 19/34; G01N 33/22; C07H 19/00; C07H 21/00
(52) U.S. Cl. .......................... 435/6; 435/91.2; 436/94; 536/22.1; 536/25.32; 536/26.6; 536/26.74
(58) Field of Search ................... 435/6, 91.2; 536/22.1, 536/25.32, 26.6, 20.74; 436/94

(56) References Cited

U.S. PATENT DOCUMENTS 5,403,708 A * 4/1995 Brennaan et al. ............. 435/94
5,908,745 A * 6/1999 Mirzabekov et al. .......... 435/6

FOREIGN PATENT DOCUMENTS

WO 89/10977 * 11/1989 ............. C12Q/1/68

OTHER PUBLICATIONS

Khrapko et al. A method for DNA sequencing by hybridization with oligonucleotide matrix, DNA Sequence, vol. 1, p. 375–388, 1991.*

* cited by examiner

*Primary Examiner*—Gary Benzion
*Assistant Examiner*—Joyce Tung
(74) *Attorney, Agent, or Firm*—Cherskov & Flaynik

(57) ABSTRACT

A method for detecting disease-associated alleles in patient genetic material is provided whereby a first group of oligonucleotide molecules, synthesized to compliment base sequences of the disease associated alleles is immobilized on a predetermined position on a substrate, and then contacted with patient genetic material to form duplexes. The duplexes are then contacted with a second group of oligonucleotide molecules which are synthesized to extend the predetermined length of the oligonucleotide molecules of the first group, and where each of the oligonucleotide molecules of the second group are tagged and either incorporate universal bases or a mixture of guanine, cytosine, thymine, and adenine, or complementary nucleotide strands that are tagged with a different fluorochrome which radiates light at a predetermined wavelength. The treated substrate is then washed and the light patterns radiating therefrom are compared with predetermined light patterns of various diseases that were prepared on identical substrates. A method is also provided for determining the length of a repeat sequence in DNA or RNA, and also for determining the base sequence of unknown DNA or RNA.

14 Claims, 6 Drawing Sheets

Fig. 5

|   |   |   |
|---|---|---|
|   | HYBRIDIZED 21-MER |   |
| -1. | 5'-TGGGCAGGTTGGTGTATCAAGGT-3' | SEQ ID NO. 10 |
|   | 3'-gel-CCGTCCAA-5' | SEQ ID NO. 11 |
| 1. | 3'-gel-CGTCCAACCATA*G̑TTCCA**-5' | SEQ ID NO. 12 |
| 2. | 3'-gel-GTCCAA*C*C-5' | SEQ ID NO. 13 |
| 3. | 3'-gel-TCCAA*C*CA-5' | SEQ ID NO. 14 |
| 4. | 3'-gel-CCAACCAT-5' | SEQ ID NO. 15 |
| 5. | 3'-gel-CAACCATA-5' | SEQ ID NO. 16 |
| +1. | 3'-gel-AACCATAGTTCCA*-5' | SEQ ID NO. 17 |

*ITALIC* -pentamers
\* -HEX
^ -FAM

| 1t | 1C |
|----|----|
| 2t | 2C |
| 3t | 3C |
| -1 | 4  |
| +1 | 5  |

FAM     HEX

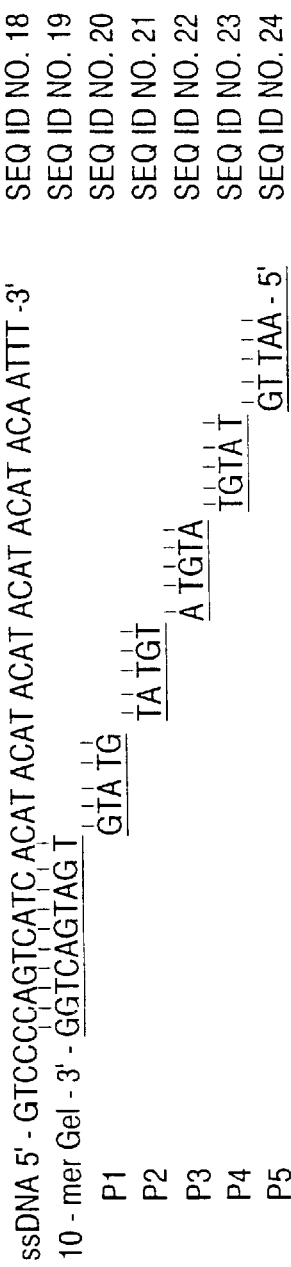
Fig. 6a
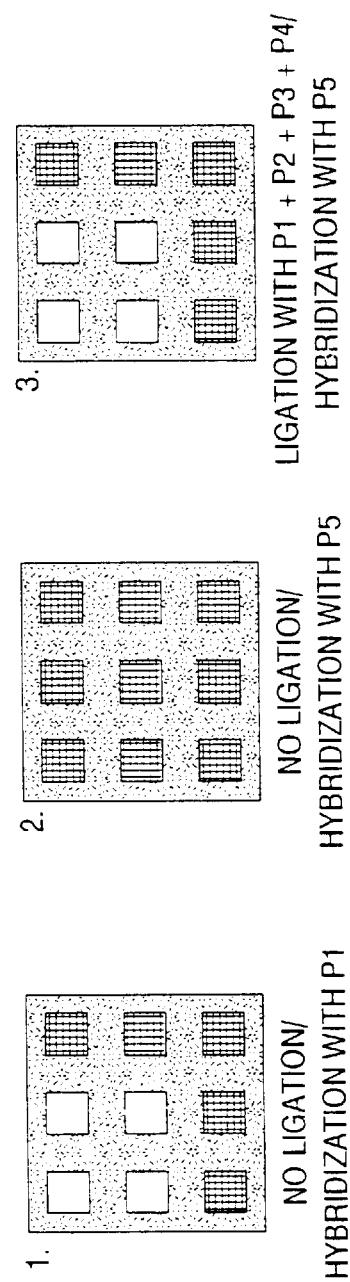
Fig. 6b
Fig. 6c

Fig. 8

CTAAGTGTGGCGGAACTACGTCCTCTAACAAGAGATGTGGCGGAACTACGTCACGTCCTCTAACAAGAGAGGACT SEQ ID NO. 71

| | | | |
|---|---|---|---|
| 1. CTAAGTG 2 SEQ ID NO. 25 | 13. GAACTAC 14 SEQ ID NO. 37 | 25. CTAACAA 26 SEQ ID NO. 49 | 37. ACGTCAC 38 SEQ ID NO. 61 |
| 2. TAAGTGT 3 SEQ ID NO. 26 | 14. AACTACG 15 SEQ ID NO. 38 | 26. TAACAAG 27 SEQ ID NO. 50 | 38. CGTCACG 39 SEQ ID NO. 62 |
| 3. AAGTGTG 4 SEQ ID NO. 27 | 15. ACTACGT 16 SEQ ID NO. 39 | 27. AACAAGA 28 SEQ ID NO. 51 | 39. GTCACGT 40 SEQ ID NO. 63 |
| 4. AGTGTGG 5 SEQ ID NO. 28 | 16. CTACGTC 17 36 SEQ ID NO. 40 | 28. ACAAGAG 29 SEQ ID NO. 52 | 40. TCACGTC 41 SEQ ID NO. 64 |
| 5. GTGTGGC 6 SEQ ID NO. 29 | 17. TACGTCC 18 SEQ ID. NO. 41 | 29. CAAGAGA 30 42 SEQ ID NO. 53 | 41. CACGTCC 18 SEQ ID NO. 65 |
| 6. TGTGGCG 7 SEQ ID NO. 30 | 18. ACGTCCT 19 SEQ ID NO. 42 | 30. AAGAGAT 31 SEQ ID NO. 54 | 42. AAGAGAG 43 SEQ ID NO. 66 |
| 7. GTGGCGG 8 SEQ ID NO. 31 | 19. CGTCCTC 20 SEQ ID NO. 43 | 31. AGAGATG 32 SEQ ID NO. 55 | 43. AGAGAGG 44 SEQ ID NO. 67 |
| 8. TGGCGGA 9 SEQ ID NO. 32 | 20. GTCCTCT 21 SEQ ID NO. 44 | 32. GAGATGT 33 SEQ ID NO. 56 | 44. GAGAGGA 45 SEQ ID NO. 68 |
| 9. GGCGGAA 10 SEQ ID NO. 33 | 21. TCCTCTA 22 SEQ ID NO. 45 | 33. AGATGTG 34 SEQ ID NO. 57 | 45. AGAGGAC 46 SEQ ID NO. 69 |
| 10. GCGGAAC 11 SEQ ID NO. 34 | 22. CCTCTAA 23 SEQ ID NO. 46 | 34. GATGTGG 35 SEQ ID NO. 58 | 46. GAGGACT SEQ ID NO. 70 |
| 11. CGGAACT 12 SEQ ID NO. 35 | 23. CTCTAAC 24 SEQ ID NO. 47 | 35. ATGTGGC 6 SEQ ID NO. 59 | |
| 12. GGAACTA 13 SEQ ID NO. 36 | 24. TCTAACA 25 SEQ ID NO. 48 | 36. TACGTCA 37 SEQ ID NO. 60 | |

SUBFRAGMENT LIST PRODUCED FROM HYBRIDIZATION STEP

| FRAGMENT NO. | FREQUENCY | FRAGMENT NOs. BEFORE | FRAGMENT SEQUENCE | | FRAGMENT NOs. AFTER |
|---|---|---|---|---|---|
| 1 | 2 | 7,4 | ACGTCCTAACAAGAGA | SEQ ID NO. 72 | 3,5 |
| 2 | 2 | 6,3 | TGTGGCGGAACTACGTC | SEQ ID NO. 73 | 7,4 |
| 3 | 1 | 1,0 | CAAGAGATGTGGCG | SEQ ID NO. 74 | 1,0 |
| 4 | 1 | 2,0 | CTACGTCACGTCCT | SEQ ID NO. 75 | 1,0 |
| 5 | 1 | 1,0 | CAAGAGAGGACT | SEQ ID NO. 76 | 0,0 |
| 6 | 1 | 0,0 | CTAAGTGTGGCG | SEQ ID NO. 77 | 2,0 |
| 7 | 1 | 2,0 | CTACGTCCT | SEQ ID NO. 78 | 1,0 |

CTAAGTGTGGCGGAACTACGTCCTCTAACAAGAGATGTGGCGGAACTACGTCACGTCCTCTAACAAGAGAGGACT SEQ ID NO. 79
  6   2         4              1              3                2                  5

CTAAGTGTGGCGGAACTACGTCCTCTAACAAGAGATGTGGCGGAACTACGTCCTCTAACAAGAGAGGACT SEQ ID NO. 80
  6   2         4              1              3                        5

SEQUENCE LISTING (1) GENERAL INFORMATION:

(iii) NUMBER OF SEQUENCES: 88

(2) INFORMATION FOR SEQ ID NO: 1:

(i) SEQUENCE CHARACTERISTICS:

```
        (A) LENGTH: 19 bases
        (B) TYPE:   nucleic acid
        (C) STRANDEDNESS: Not Applicable
        (D) TOPOLOGY: linear (ii) MOLECULE TYPE:Genomic DNA (iii) HYPOTHETICAL: yes (xi) SEQUENCE DESCRIPTION: SEQ ID NO: 1:

CCTGGGCAGG TTGGTATCA                                            19

(2) INFORMATION FOR SEQ ID NO: 2:

(i) SEQUENCE CHARACTERISTICS:
        (A) LENGTH: 8 bases
        (B) TYPE:   nucleic acid
        (C) STRANDEDNESS: Not Applicable
        (D) TOPOLOGY: linear (ii) MOLECULE TYPE:Genomic DNA (iii) HYPOTHETICAL: yes (xi) SEQUENCE DESCRIPTION: SEQ ID NO: 2:

TGCCCAGG                                                        8

(2) INFORMATION FOR SEQ ID NO: 3:

(i) SEQUENCE CHARACTERISTICS:
        (A) LENGTH: 5 bases
        (B) TYPE:   nucleic acid
        (C) STRANDEDNESS: Not Applicable
        (D) TOPOLOGY: linear (ii) MOLECULE TYPE:Genomic DNA (iii) HYPOTHETICAL: yes (xi) SEQUENCE DESCRIPTION: SEQ ID NO: 3:

CAACC                                                           5

(2) INFORMATION FOR SEQ ID NO: 4:

(i) SEQUENCE CHARACTERISTICS:
        (A) LENGTH: 5 bases
        (B) TYPE:   nucleic acid
        (C) STRANDEDNESS: Not Applicable
        (D) TOPOLOGY: linear (ii) MOLECULE TYPE:Genomic DNA (iii) HYPOTHETICAL: yes (xi) SEQUENCE DESCRIPTION: SEQ ID NO: 4:

CAAGC                                                           5

(2) INFORMATION FOR SEQ ID NO: 5:

(i) SEQUENCE CHARACTERISTICS:
        (A) LENGTH: 5 bases
        (B) TYPE:   nucleic acid
        (C) STRANDEDNESS: Not Applicable
        (D) TOPOLOGY: linear (ii) MOLECULE TYPE:Genomic DNA (iii) HYPOTHETICAL: yes (xi) SEQUENCE DESCRIPTION: SEQ ID NO: 5:
```

```
CAACC                                                                    5

(2) INFORMATION FOR SEQ ID NO: 6:

(i) SEQUENCE CHARACTERISTICS:
        (A) LENGTH: 8 bases
        (B) TYPE:   nucleic acid
        (C) STRANDEDNESS: Not Applicable
        (D) TOPOLOGY: linear (ii) MOLECULE TYPE:Genomic DNA (iii) HYPOTHETICAL: yes (xi) SEQUENCE DESCRIPTION: SEQ ID NO: 6:

CTGCCCAG                                                                 8

(2) INFORMATION FOR SEQ ID NO: 7:

(i) SEQUENCE CHARACTERISTICS:
        (A) LENGTH: 5 bases
        (B) TYPE:   nucleic acid
        (C) STRANDEDNESS: Not Applicable
        (D) TOPOLOGY: linear (ii) MOLECULE TYPE:Genomic DNA (iii) HYPOTHETICAL: yes (xi) SEQUENCE DESCRIPTION: SEQ ID NO: 7:

CCAAC                                                                    5

(2) INFORMATION FOR SEQ ID NO: 8:

(i) SEQUENCE CHARACTERISTICS:
        (A) LENGTH: 5 bases
        (B) TYPE:   nucleic acid
        (C) STRANDEDNESS: Not Applicable
        (D) TOPOLOGY: linear (ii) MOLECULE TYPE:Genomic DNA (iii) HYPOTHETICAL: yes (xi) SEQUENCE DESCRIPTION: SEQ ID NO: 8:

CCAAC                                                                    5

(2) INFORMATION FOR SEQ ID NO: 9:

(i) SEQUENCE CHARACTERISTICS:
        (A) LENGTH: 5 bases
        (B) TYPE:   nucleic acid
        (C) STRANDEDNESS: Not Applicable
        (D) TOPOLOGY: linear (ii) MOLECULE TYPE:Genomic DNA (iii) HYPOTHETICAL: yes (xi) SEQUENCE DESCRIPTION: SEQ ID NO: 9:

CCAAA                                                                    5

(2) INFORMATION FOR SEQ ID NO: 10:

(i) SEQUENCE CHARACTERISTICS:
        (A) LENGTH: 21 bases
        (B) TYPE:   nucleic acid
        (C) STRANDEDNESS: Not Applicable
        (D) TOPOLOGY: linear
```

(ii) MOLECULE TYPE:Genomic DNA (iii) HYPOTHETICAL: yes (xi) SEQUENCE DESCRIPTION: SEQ ID NO: 10:

TGGGCAGGTT GGTATCAAGG T                                                    21

(2) INFORMATION FOR SEQ ID NO: 11:

(i) SEQUENCE CHARACTERISTICS:
            (A) LENGTH: 8 bases
            (B) TYPE:  nucleic acid
            (C) STRANDEDNESS: Not Applicable
            (D) TOPOLOGY: linear (ii) MOLECULE TYPE:Genomic DNA (iii) HYPOTHETICAL: yes (xi) SEQUENCE DESCRIPTION: SEQ ID NO: 11:

AACCTGCC                                                                    8

(2) INFORMATION FOR SEQ ID NO: 12:

(i) SEQUENCE CHARACTERISTICS:
            (A) LENGTH:  18 bases
            (B) TYPE:  nucleic acid
            (C) STRANDEDNESS: Not Applicable
            (D) TOPOLOGY: linear (ii) MOLECULE TYPE:Genomic DNA (iii) HYPOTHETICAL: yes (xi) SEQUENCE DESCRIPTION: SEQ ID NO: 12:

ACCTTGATAC CAACCTGC                                                        18

(2) INFORMATION FOR SEQ ID NO: 13:

(i) SEQUENCE CHARACTERISTICS:
            (A) LENGTH: 8 bases
            (B) TYPE:  nucleic acid
            (C) STRANDEDNESS: Not Applicable
            (D) TOPOLOGY: linear (ii) MOLECULE TYPE:Genomic DNA (iii) HYPOTHETICAL: yes (xi) SEQUENCE DESCRIPTION: SEQ ID NO: 13:

CCAACCTG                                                                    8

(2) INFORMATION FOR SEQ ID NO: 14:

(i) SEQUENCE CHARACTERISTICS:
            (A) LENGTH: 8 bases
            (B) TYPE:  nucleic acid
            (C) STRANDEDNESS: Not Applicable
            (D) TOPOLOGY: linear (ii) MOLECULE TYPE:Genomic DNA (iii) HYPOTHETICAL: yes (xi) SEQUENCE DESCRIPTION: SEQ ID NO: 14:

ACCAACCT                                                                    8

(2) INFORMATION FOR SEQ ID NO: 15:

(i) SEQUENCE CHARACTERISTICS:
            (A) LENGTH: 8 bases
            (B) TYPE:   nucleic acid
            (C) STRANDEDNESS: Not Applicable
            (D) TOPOLOGY: linear (ii) MOLECULE TYPE:Genomic DNA (iii) HYPOTHETICAL: yes (xi) SEQUENCE DESCRIPTION: SEQ ID NO: 15:

TACCAACC                                                                  8

(2) INFORMATION FOR SEQ ID NO: 16:

(i) SEQUENCE CHARACTERISTICS:
            (A) LENGTH: 8 bases
            (B) TYPE:   nucleic acid
            (C) STRANDEDNESS: Not Applicable
            (D) TOPOLOGY: linear (ii) MOLECULE TYPE:Genomic DNA (iii) HYPOTHETICAL: yes (xi) SEQUENCE DESCRIPTION: SEQ ID NO: 16:

ATACCAAC                                                                  8

(2) INFORMATION FOR SEQ ID NO: 17:

(i) SEQUENCE CHARACTERISTICS:
            (A) LENGTH:  13 bases
            (B) TYPE:   nucleic acid
            (C) STRANDEDNESS: Not Applicable
            (D) TOPOLOGY: linear (ii) MOLECULE TYPE:Genomic DNA (iii) HYPOTHETICAL: yes (xi) SEQUENCE DESCRIPTION: SEQ ID NO: 17:

ACCTTGATAC CAA                                                           13

(2) INFORMATION FOR SEQ ID NO: 18:

(i) SEQUENCE CHARACTERISTICS:
            (A) LENGTH: 40 bases
            (B) TYPE:   nucleic acid
            (C) STRANDEDNESS: Not Applicable
            (D) TOPOLOGY: linear (ii) MOLECULE TYPE:Genomic DNA (iii) HYPOTHETICAL: yes (xi) SEQUENCE DESCRIPTION: SEQ ID NO: 18:

GTCCCCAGTC ATCACATACA TACATACATA CATACAATTT                              40

(2) INFORMATION FOR SEQ ID NO: 19:

(i) SEQUENCE CHARACTERISTICS:
            (A) LENGTH: 10 bases
            (B) TYPE:   nucleic acid
            (C) STRANDEDNESS: Not Applicable
            (D) TOPOLOGY: linear (ii) MOLECULE TYPE:Genomic DNA (iii) HYPOTHETICAL: yes (xi) SEQUENCE DESCRIPTION: SEQ ID NO: 19:

TGATGACTGG 10

(2) INFORMATION FOR SEQ ID NO: 20:

(i) SEQUENCE CHARACTERISTICS:
        (A) LENGTH: 5 bases
        (B) TYPE: nucleic acid
        (C) STRANDEDNESS: Not Applicable
        (D) TOPOLOGY: linear (ii) MOLECULE TYPE:Genomic DNA (iii) HYPOTHETICAL: yes (xi) SEQUENCE DESCRIPTION: SEQ ID NO: 20:

GTATG 5

(2) INFORMATION FOR SEQ ID NO: 21:

(i) SEQUENCE CHARACTERISTICS:
        (A) LENGTH: 5 bases
        (B) TYPE: nucleic acid
        (C) STRANDEDNESS: Not Applicable
        (D) TOPOLOGY: linear (ii) MOLECULE TYPE:Genomic DNA (iii) HYPOTHETICAL: yes (xi) SEQUENCE DESCRIPTION: SEQ ID NO: 21:

TGTAT 5

(2) INFORMATION FOR SEQ ID NO: 22:

(i) SEQUENCE CHARACTERISTICS:
        (A) LENGTH: 5 bases
        (B) TYPE: nucleic acid
        (C) STRANDEDNESS: Not Applicable
        (D) TOPOLOGY: linear (ii) MOLECULE TYPE:Genomic DNA (iii) HYPOTHETICAL: yes (xi) SEQUENCE DESCRIPTION: SEQ ID NO: 22:

ATGTA 5

(2) INFORMATION FOR SEQ ID NO: 23:

(i) SEQUENCE CHARACTERISTICS:
        (A) LENGTH: 5 bases
        (B) TYPE: nucleic acid
        (C) STRANDEDNESS: Not Applicable
        (D) TOPOLOGY: linear (ii) MOLECULE TYPE:Genomic DNA (iii) HYPOTHETICAL: yes (xi) SEQUENCE DESCRIPTION: SEQ ID NO: 23:

TATGT 5

(2) INFORMATION FOR SEQ ID NO: 24:

(i) SEQUENCE CHARACTERISTICS:
        (A) LENGTH: 5 bases
        (B) TYPE: nucleic acid
        (C) STRANDEDNESS: Not Applicable
        (D) TOPOLOGY: linear (ii) MOLECULE TYPE:Genomic DNA (iii) HYPOTHETICAL: yes (xi) SEQUENCE DESCRIPTION: SEQ ID NO: 24:

AATTG                                                                                            5

(2) INFORMATION FOR SEQ ID NO: 25:

(i) SEQUENCE CHARACTERISTICS:
              (A) LENGTH: 7 bases
              (B) TYPE:  nucleic acid
              (C) STRANDEDNESS: Not Applicable
              (D) TOPOLOGY: linear (ii) MOLECULE TYPE:Genomic DNA (iii) HYPOTHETICAL: yes (xi) SEQUENCE DESCRIPTION: SEQ ID NO: 25:

CTAAGTG                                                                                          7

(2) INFORMATION FOR SEQ ID NO: 26:

(i) SEQUENCE CHARACTERISTICS:
              (A) LENGTH: 7 bases
              (B) TYPE:  nucleic acid
              (C) STRANDEDNESS: Not Applicable
              (D) TOPOLOGY: linear (ii) MOLECULE TYPE:Genomic DNA (iii) HYPOTHETICAL: yes (xi) SEQUENCE DESCRIPTION: SEQ ID NO: 26:

TAAGTGT                                                                                          7

(2) INFORMATION FOR SEQ ID NO: 27:

(i) SEQUENCE CHARACTERISTICS:
              (A) LENGTH: 7 bases
              (B) TYPE:  nucleic acid
              (C) STRANDEDNESS: Not Applicable
              (D) TOPOLOGY: linear (ii) MOLECULE TYPE:Genomic DNA (iii) HYPOTHETICAL: yes (xi) SEQUENCE DESCRIPTION: SEQ ID NO: 27:

AAGTGTG                                                                                          7

(2) INFORMATION FOR SEQ ID NO: 28:

(i) SEQUENCE CHARACTERISTICS:
              (A) LENGTH: 7 bases
              (B) TYPE:  nucleic acid
              (C) STRANDEDNESS: Not Applicable
              (D) TOPOLOGY: linear (ii) MOLECULE TYPE:Genomic DNA (iii) HYPOTHETICAL: yes (xi) SEQUENCE DESCRIPTION: SEQ ID NO: 28:

AGTGTGG                                                                                          7

(2) INFORMATION FOR SEQ ID NO: 29:

```
      (i) SEQUENCE CHARACTERISTICS:
           (A) LENGTH: 7 bases
           (B) TYPE:   nucleic acid
           (C) STRANDEDNESS: Not Applicable
           (D) TOPOLOGY: linear (ii) MOLECULE TYPE:Genomic DNA (iii) HYPOTHETICAL: yes (xi) SEQUENCE DESCRIPTION: SEQ ID NO: 29:

GTGTGGC                                                                7

(2) INFORMATION FOR SEQ ID NO: 30:

(i) SEQUENCE CHARACTERISTICS:
           (A) LENGTH: 7 bases
           (B) TYPE:   nucleic acid
           (C) STRANDEDNESS: Not Applicable
           (D) TOPOLOGY: linear (ii) MOLECULE TYPE:Genomic DNA (iii) HYPOTHETICAL: yes (xi) SEQUENCE DESCRIPTION: SEQ ID NO: 30:

TGTGGCG                                                                7

(2) INFORMATION FOR SEQ ID NO: 31:

(i) SEQUENCE CHARACTERISTICS:
           (A) LENGTH: 7 bases
           (B) TYPE:   nucleic acid
           (C) STRANDEDNESS: Not Applicable
           (D) TOPOLOGY: linear (ii) MOLECULE TYPE:Genomic DNA (iii) HYPOTHETICAL: yes (xi) SEQUENCE DESCRIPTION: SEQ ID NO: 31:

GTGGCGG                                                                7

(2) INFORMATION FOR SEQ ID NO: 32:

(i) SEQUENCE CHARACTERISTICS:
           (A) LENGTH: 7 bases
           (B) TYPE:   nucleic acid
           (C) STRANDEDNESS: Not Applicable
           (D) TOPOLOGY: linear (ii) MOLECULE TYPE:Genomic DNA (iii) HYPOTHETICAL: yes (xi) SEQUENCE DESCRIPTION: SEQ ID NO: 32:

TGGCGGA                                                                7

(2) INFORMATION FOR SEQ ID NO: 33:

(i) SEQUENCE CHARACTERISTICS:
           (A) LENGTH: 7 bases
           (B) TYPE:   nucleic acid
           (C) STRANDEDNESS: Not Applicable
           (D) TOPOLOGY: linear (ii) MOLECULE TYPE:Genomic DNA (iii) HYPOTHETICAL: yes
```

```
        (xi) SEQUENCE DESCRIPTION: SEQ ID NO: 33:

GGCGGAA                                                             7

(2) INFORMATION FOR SEQ ID NO: 34:

(i) SEQUENCE CHARACTERISTICS:
        (A) LENGTH: 7 bases
        (B) TYPE:  nucleic acid
        (C) STRANDEDNESS: Not Applicable
        (D) TOPOLOGY: linear (ii) MOLECULE TYPE:Genomic DNA (iii) HYPOTHETICAL: yes (xi) SEQUENCE DESCRIPTION: SEQ ID NO: 34:

GCGGAAC                                                             7

(2) INFORMATION FOR SEQ ID NO: 35:

(i) SEQUENCE CHARACTERISTICS:
        (A) LENGTH: 7 bases
        (B) TYPE:  nucleic acid
        (C) STRANDEDNESS: Not Applicable
        (D) TOPOLOGY: linear (ii) MOLECULE TYPE:Genomic DNA (iii) HYPOTHETICAL: yes (xi) SEQUENCE DESCRIPTION: SEQ ID NO: 35:

CGGAACT                                                             7

(2) INFORMATION FOR SEQ ID NO: 36:

(i) SEQUENCE CHARACTERISTICS:
        (A) LENGTH: 7 bases
        (B) TYPE:  nucleic acid
        (C) STRANDEDNESS: Not Applicable
        (D) TOPOLOGY: linear (ii) MOLECULE TYPE:Genomic DNA (iii) HYPOTHETICAL: yes (xi) SEQUENCE DESCRIPTION: SEQ ID NO: 36:

GGAACTA                                                             7

(2) INFORMATION FOR SEQ ID NO: 37:

(i) SEQUENCE CHARACTERISTICS:
        (A) LENGTH: 7 bases
        (B) TYPE:  nucleic acid
        (C) STRANDEDNESS: Not Applicable
        (D) TOPOLOGY: linear (ii) MOLECULE TYPE:Genomic DNA (iii) HYPOTHETICAL: yes (xi) SEQUENCE DESCRIPTION: SEQ ID NO: 37:

GAACTAC                                                             7

(2) INFORMATION FOR SEQ ID NO: 38:

(i) SEQUENCE CHARACTERISTICS:
        (A) LENGTH: 7 bases
        (B) TYPE:  nucleic acid
        (C) STRANDEDNESS: Not Applicable
```

```
        (D) TOPOLOGY: linear (ii) MOLECULE TYPE:Genomic DNA (iii) HYPOTHETICAL: yes (xi) SEQUENCE DESCRIPTION: SEQ ID NO: 38:

AACTACG                                                               7

(2) INFORMATION FOR SEQ ID NO: 39:

(i) SEQUENCE CHARACTERISTICS:
        (A) LENGTH: 7 bases
        (B) TYPE:   nucleic acid
        (C) STRANDEDNESS: Not Applicable
        (D) TOPOLOGY: linear (ii) MOLECULE TYPE:Genomic DNA (iii) HYPOTHETICAL: yes (xi) SEQUENCE DESCRIPTION: SEQ ID NO: 39:

ACTACGT                                                               7

(2) INFORMATION FOR SEQ ID NO: 40:

(i) SEQUENCE CHARACTERISTICS:
        (A) LENGTH: 7 bases
        (B) TYPE:   nucleic acid
        (C) STRANDEDNESS: Not Applicable
        (D) TOPOLOGY: linear (ii) MOLECULE TYPE:Genomic DNA (iii) HYPOTHETICAL: yes (xi) SEQUENCE DESCRIPTION: SEQ ID NO: 40:

CTACGTC                                                               7

(2) INFORMATION FOR SEQ ID NO: 41:

(i) SEQUENCE CHARACTERISTICS:
        (A) LENGTH: 7 bases
        (B) TYPE:   nucleic acid
        (C) STRANDEDNESS: Not Applicable
        (D) TOPOLOGY: linear (ii) MOLECULE TYPE:Genomic DNA (iii) HYPOTHETICAL: yes (xi) SEQUENCE DESCRIPTION: SEQ ID NO: 41:

TACGTCC                                                               7

(2) INFORMATION FOR SEQ ID NO: 42:

(i) SEQUENCE CHARACTERISTICS:
        (A) LENGTH: 7 bases
        (B) TYPE:   nucleic acid
        (C) STRANDEDNESS: Not Applicable
        (D) TOPOLOGY: linear (ii) MOLECULE TYPE:Genomic DNA (iii) HYPOTHETICAL: yes (xi) SEQUENCE DESCRIPTION: SEQ ID NO: 42:

ACGTCCT                                                               7
```

(2) INFORMATION FOR SEQ ID NO: 43:

(i) SEQUENCE CHARACTERISTICS:
        (A) LENGTH: 7 bases
        (B) TYPE:  nucleic acid
        (C) STRANDEDNESS: Not Applicable
        (D) TOPOLOGY: linear (ii) MOLECULE TYPE:Genomic DNA (iii) HYPOTHETICAL: yes (xi) SEQUENCE DESCRIPTION: SEQ ID NO: 43:

CGTCCTC      7

(2) INFORMATION FOR SEQ ID NO: 44:

(i) SEQUENCE CHARACTERISTICS:
        (A) LENGTH: 7 bases
        (B) TYPE:  nucleic acid
        (C) STRANDEDNESS: Not Applicable
        (D) TOPOLOGY: linear (ii) MOLECULE TYPE:Genomic DNA (iii) HYPOTHETICAL: yes (xi) SEQUENCE DESCRIPTION: SEQ ID NO: 44:

GTCCTCT      7

(2) INFORMATION FOR SEQ ID NO: 45:

(i) SEQUENCE CHARACTERISTICS:
        (A) LENGTH: 7 bases
        (B) TYPE:  nucleic acid
        (C) STRANDEDNESS: Not Applicable
        (D) TOPOLOGY: linear (ii) MOLECULE TYPE:Genomic DNA (iii) HYPOTHETICAL: yes (xi) SEQUENCE DESCRIPTION: SEQ ID NO: 45:

TCCTCTA      7

(2) INFORMATION FOR SEQ ID NO: 46:

(i) SEQUENCE CHARACTERISTICS:
        (A) LENGTH: 7 bases
        (B) TYPE:  nucleic acid
        (C) STRANDEDNESS: Not Applicable
        (D) TOPOLOGY: linear (ii) MOLECULE TYPE:Genomic DNA (iii) HYPOTHETICAL: yes (xi) SEQUENCE DESCRIPTION: SEQ ID NO: 46:

CCTCTAA      7

(2) INFORMATION FOR SEQ ID NO: 47:

(i) SEQUENCE CHARACTERISTICS:
        (A) LENGTH: 7 bases
        (B) TYPE:  nucleic acid
        (C) STRANDEDNESS: Not Applicable
        (D) TOPOLOGY: linear (ii) MOLECULE TYPE:Genomic DNA (iii) HYPOTHETICAL: yes (xi) SEQUENCE DESCRIPTION: SEQ ID NO: 47:

CTCTAAC                                                                  7

(2) INFORMATION FOR SEQ ID NO: 48:

(i) SEQUENCE CHARACTERISTICS:
          (A) LENGTH: 7 bases
          (B) TYPE:   nucleic acid
          (C) STRANDEDNESS: Not Applicable
          (D) TOPOLOGY: linear (ii) MOLECULE TYPE:Genomic DNA (iii) HYPOTHETICAL: yes (xi) SEQUENCE DESCRIPTION: SEQ ID NO: 48:

TCTAACA                                                                  7

(2) INFORMATION FOR SEQ ID NO: 49:

(i) SEQUENCE CHARACTERISTICS:
          (A) LENGTH: 7 bases
          (B) TYPE:   nucleic acid
          (C) STRANDEDNESS: Not Applicable
          (D) TOPOLOGY: linear (ii) MOLECULE TYPE:Genomic DNA (iii) HYPOTHETICAL: yes (xi) SEQUENCE DESCRIPTION: SEQ ID NO: 49:

CTAACAA                                                                  7

(2) INFORMATION FOR SEQ ID NO: 50:

(i) SEQUENCE CHARACTERISTICS:
          (A) LENGTH: 7 bases
          (B) TYPE:   nucleic acid
          (C) STRANDEDNESS: Not Applicable
          (D) TOPOLOGY: linear (ii) MOLECULE TYPE:Genomic DNA (iii) HYPOTHETICAL: yes (xi) SEQUENCE DESCRIPTION: SEQ ID NO: 50:

TAACAAG                                                                  7

(2) INFORMATION FOR SEQ ID NO: 51:

(i) SEQUENCE CHARACTERISTICS:
          (A) LENGTH: 7 bases
          (B) TYPE:   nucleic acid
          (C) STRANDEDNESS: Not Applicable
          (D) TOPOLOGY: linear (ii) MOLECULE TYPE:Genomic DNA (iii) HYPOTHETICAL: yes (xi) SEQUENCE DESCRIPTION: SEQ ID NO: 51:

AACAAGA                                                                  7

(2) INFORMATION FOR SEQ ID NO: 52:

(i) SEQUENCE CHARACTERISTICS:
          (A) LENGTH: 7 bases
          (B) TYPE:   nucleic acid

```
            (C) STRANDEDNESS: Not Applicable
            (D) TOPOLOGY: linear (ii) MOLECULE TYPE:Genomic DNA (iii) HYPOTHETICAL: yes (xi) SEQUENCE DESCRIPTION: SEQ ID NO: 52:

ACAAGAG                                                                          7

(2) INFORMATION FOR SEQ ID NO: 53:

(i) SEQUENCE CHARACTERISTICS:
            (A) LENGTH: 7 bases
            (B) TYPE:  nucleic acid
            (C) STRANDEDNESS: Not Applicable
            (D) TOPOLOGY: linear (ii) MOLECULE TYPE:Genomic DNA (iii) HYPOTHETICAL: yes (xi) SEQUENCE DESCRIPTION: SEQ ID NO: 53:

CAAGAGA                                                                          7

(2) INFORMATION FOR SEQ ID NO: 54:

(i) SEQUENCE CHARACTERISTICS:
            (A) LENGTH: 7 bases
            (B) TYPE:  nucleic acid
            (C) STRANDEDNESS: Not Applicable
            (D) TOPOLOGY: linear (ii) MOLECULE TYPE:Genomic DNA (iii) HYPOTHETICAL: yes (xi) SEQUENCE DESCRIPTION: SEQ ID NO: 54:

AAGAGAT                                                                          7

(2) INFORMATION FOR SEQ ID NO: 55:

(i) SEQUENCE CHARACTERISTICS:
            (A) LENGTH: 7 bases
            (B) TYPE:  nucleic acid
            (C) STRANDEDNESS: Not Applicable
            (D) TOPOLOGY: linear (ii) MOLECULE TYPE:Genomic DNA (iii) HYPOTHETICAL: yes (xi) SEQUENCE DESCRIPTION: SEQ ID NO: 55:

AGAGATG                                                                          7

(2) INFORMATION FOR SEQ ID NO: 56:

(i) SEQUENCE CHARACTERISTICS:
            (A) LENGTH: 7 bases
            (B) TYPE:  nucleic acid
            (C) STRANDEDNESS: Not Applicable
            (D) TOPOLOGY: linear (ii) MOLECULE TYPE:Genomic DNA (iii) HYPOTHETICAL: yes (xi) SEQUENCE DESCRIPTION: SEQ ID NO: 56:

GAGATGT                                                                          7
```

(2) INFORMATION FOR SEQ ID NO: 57:

(i) SEQUENCE CHARACTERISTICS:
        (A) LENGTH: 7 bases
        (B) TYPE: nucleic acid
        (C) STRANDEDNESS: Not Applicable
        (D) TOPOLOGY: linear (ii) MOLECULE TYPE: Genomic DNA (iii) HYPOTHETICAL: yes (xi) SEQUENCE DESCRIPTION: SEQ ID NO: 57:

AGATGTG    7

(2) INFORMATION FOR SEQ ID NO: 58:

(i) SEQUENCE CHARACTERISTICS:
        (A) LENGTH: 7 bases
        (B) TYPE: nucleic acid
        (C) STRANDEDNESS: Not Applicable
        (D) TOPOLOGY: linear (ii) MOLECULE TYPE: Genomic DNA (iii) HYPOTHETICAL: yes (xi) SEQUENCE DESCRIPTION: SEQ ID NO: 58:

GATGTGG    7

(2) INFORMATION FOR SEQ ID NO: 59:

(i) SEQUENCE CHARACTERISTICS:
        (A) LENGTH: 7 bases
        (B) TYPE: nucleic acid
        (C) STRANDEDNESS: Not Applicable
        (D) TOPOLOGY: linear (ii) MOLECULE TYPE: Genomic DNA (iii) HYPOTHETICAL: yes (xi) SEQUENCE DESCRIPTION: SEQ ID NO: 59:

ATGTGGC    7

(2) INFORMATION FOR SEQ ID NO: 60:

(i) SEQUENCE CHARACTERISTICS:
        (A) LENGTH: 7 bases
        (B) TYPE: nucleic acid
        (C) STRANDEDNESS: Not Applicable
        (D) TOPOLOGY: linear (ii) MOLECULE TYPE: Genomic DNA (iii) HYPOTHETICAL: yes (xi) SEQUENCE DESCRIPTION: SEQ ID NO: 60:

TACGTCA    7

(2) INFORMATION FOR SEQ ID NO: 61:

(i) SEQUENCE CHARACTERISTICS:
        (A) LENGTH: 7 bases
        (B) TYPE: nucleic acid
        (C) STRANDEDNESS: Not Applicable
        (D) TOPOLOGY: linear (ii) MOLECULE TYPE: Genomic DNA

```
        (iii) HYPOTHETICAL: yes (xi) SEQUENCE DESCRIPTION: SEQ ID NO: 61:

ACGTCAC                                                           7

(2) INFORMATION FOR SEQ ID NO: 62:

(i) SEQUENCE CHARACTERISTICS:
            (A) LENGTH: 7 bases
            (B) TYPE:   nucleic acid
            (C) STRANDEDNESS: Not Applicable
            (D) TOPOLOGY: linear (ii) MOLECULE TYPE:Genomic DNA (iii) HYPOTHETICAL: yes (xi) SEQUENCE DESCRIPTION: SEQ ID NO: 62:

CGTCACG                                                           7

(2) INFORMATION FOR SEQ ID NO: 63:

(i) SEQUENCE CHARACTERISTICS:
            (A) LENGTH: 7 bases
            (B) TYPE:   nucleic acid
            (C) STRANDEDNESS: Not Applicable
            (D) TOPOLOGY: linear (ii) MOLECULE TYPE:Genomic DNA (iii) HYPOTHETICAL: yes (xi) SEQUENCE DESCRIPTION: SEQ ID NO: 63:

GTCACGT                                                           7

(2) INFORMATION FOR SEQ ID NO: 64:

(i) SEQUENCE CHARACTERISTICS:
            (A) LENGTH: 7 bases
            (B) TYPE:   nucleic acid
            (C) STRANDEDNESS: Not Applicable
            (D) TOPOLOGY: linear (ii) MOLECULE TYPE:Genomic DNA (iii) HYPOTHETICAL: yes (xi) SEQUENCE DESCRIPTION: SEQ ID NO: 64:

TCACGTC                                                           7

(2) INFORMATION FOR SEQ ID NO: 65:

(i) SEQUENCE CHARACTERISTICS:
            (A) LENGTH: 7 bases
            (B) TYPE:   nucleic acid
            (C) STRANDEDNESS: Not Applicable
            (D) TOPOLOGY: linear (ii) MOLECULE TYPE:Genomic DNA (iii) HYPOTHETICAL: yes (xi) SEQUENCE DESCRIPTION: SEQ ID NO: 65:

CACGTCC                                                           7

(2) INFORMATION FOR SEQ ID NO: 66:

(i) SEQUENCE CHARACTERISTICS:
            (A) LENGTH: 7 bases
```

```
        (B) TYPE:  nucleic acid
        (C) STRANDEDNESS: Not Applicable
        (D) TOPOLOGY: linear (ii) MOLECULE TYPE:Genomic DNA (iii) HYPOTHETICAL: yes (xi) SEQUENCE DESCRIPTION: SEQ ID NO: 66:

AAGAGAG                                                              7

(2) INFORMATION FOR SEQ ID NO: 67:

(i) SEQUENCE CHARACTERISTICS:
        (A) LENGTH: 7 bases
        (B) TYPE:  nucleic acid
        (C) STRANDEDNESS: Not Applicable
        (D) TOPOLOGY: linear (ii) MOLECULE TYPE:Genomic DNA (iii) HYPOTHETICAL: yes (xi) SEQUENCE DESCRIPTION: SEQ ID NO: 67:

AGAGAGG                                                              7

(2) INFORMATION FOR SEQ ID NO: 68:

(i) SEQUENCE CHARACTERISTICS:
        (A) LENGTH: 7 bases
        (B) TYPE:  nucleic acid
        (C) STRANDEDNESS: Not Applicable
        (D) TOPOLOGY: linear (ii) MOLECULE TYPE:Genomic DNA (iii) HYPOTHETICAL: yes (xi) SEQUENCE DESCRIPTION: SEQ ID NO: 68:

GAGAGGA                                                              7

(2) INFORMATION FOR SEQ ID NO: 69:

(i) SEQUENCE CHARACTERISTICS:
        (A) LENGTH: 7 bases
        (B) TYPE:  nucleic acid
        (C) STRANDEDNESS: Not Applicable
        (D) TOPOLOGY: linear (ii) MOLECULE TYPE:Genomic DNA (iii) HYPOTHETICAL: yes (xi) SEQUENCE DESCRIPTION: SEQ ID NO: 69:

AGAGGAC                                                              7

(2) INFORMATION FOR SEQ ID NO: 70:

(i) SEQUENCE CHARACTERISTICS:
        (A) LENGTH: 7 bases
        (B) TYPE:  nucleic acid
        (C) STRANDEDNESS: Not Applicable
        (D) TOPOLOGY: linear (ii) MOLECULE TYPE:Genomic DNA (iii) HYPOTHETICAL: yes (xi) SEQUENCE DESCRIPTION: SEQ ID NO: 70:

GAGGACT                                                              7
```

(2) INFORMATION FOR SEQ ID NO: 71:

(i) SEQUENCE CHARACTERISTICS:
        (A) LENGTH: 74 bases
        (B) TYPE: nucleic acid
        (C) STRANDEDNESS: Not Applicable
        (D) TOPOLOGY: linear (ii) MOLECULE TYPE: Genomic DNA (iii) HYPOTHETICAL: yes (xi) SEQUENCE DESCRIPTION: SEQ ID NO: 71:

```
CTAAGTGTGG CGGAACTACG TCCTCTAACA AGAGATGTGG CGAACTACGT CACGTCCTCT      60

AACAAGAGAG GACT                                                        74
```

(2) INFORMATION FOR SEQ ID NO: 72:

(i) SEQUENCE CHARACTERISTICS:
        (A) LENGTH: 18 bases
        (B) TYPE: nucleic acid
        (C) STRANDEDNESS: Not Applicable
        (D) TOPOLOGY: linear (ii) MOLECULE TYPE: Genomic DNA (iii) HYPOTHETICAL: yes (xi) SEQUENCE DESCRIPTION: SEQ ID NO: 72:

```
ACGTCCTCTA ACAAGAGA                                                    18
```

(2) INFORMATION FOR SEQ ID NO: 73:

(i) SEQUENCE CHARACTERISTICS:
        (A) LENGTH: 17 bases
        (B) TYPE: nucleic acid
        (C) STRANDEDNESS: Not Applicable
        (D) TOPOLOGY: linear (ii) MOLECULE TYPE: Genomic DNA (iii) HYPOTHETICAL: yes (xi) SEQUENCE DESCRIPTION: SEQ ID NO: 73:

```
TGTGGCGGAA CTACGTC                                                     17
```

(2) INFORMATION FOR SEQ ID NO: 74:

(i) SEQUENCE CHARACTERISTICS:
        (A) LENGTH: 14 bases
        (B) TYPE: nucleic acid
        (C) STRANDEDNESS: Not Applicable
        (D) TOPOLOGY: linear (ii) MOLECULE TYPE: Genomic DNA (iii) HYPOTHETICAL: yes (xi) SEQUENCE DESCRIPTION: SEQ ID NO: 74:

```
CAAGAGATGT GGCG                                                        14
```

(2) INFORMATION FOR SEQ ID NO: 75:

(i) SEQUENCE CHARACTERISTICS:
        (A) LENGTH: 14 bases
        (B) TYPE: nucleic acid
        (C) STRANDEDNESS: Not Applicable
        (D) TOPOLOGY: linear (ii) MOLECULE TYPE:Genomic DNA (iii) HYPOTHETICAL: yes (xi) SEQUENCE DESCRIPTION: SEQ ID NO: 75:

CTACGTCACG TCCT                                                              14

(2) INFORMATION FOR SEQ ID NO: 76:

(i) SEQUENCE CHARACTERISTICS:
            (A) LENGTH: 12 bases
            (B) TYPE:  nucleic acid
            (C) STRANDEDNESS: Not Applicable
            (D) TOPOLOGY: linear (ii) MOLECULE TYPE:Genomic DNA (iii) HYPOTHETICAL: yes (xi) SEQUENCE DESCRIPTION: SEQ ID NO: 76:

CAAGAGAGGA CT                                                                12

(2) INFORMATION FOR SEQ ID NO: 77:

(i) SEQUENCE CHARACTERISTICS:
            (A) LENGTH: 12 bases
            (B) TYPE:  nucleic acid
            (C) STRANDEDNESS: Not Applicable
            (D) TOPOLOGY: linear (ii) MOLECULE TYPE:Genomic DNA (iii) HYPOTHETICAL: yes (xi) SEQUENCE DESCRIPTION: SEQ ID NO: 77:

CTAAGTGTGG CG                                                                12

(2) INFORMATION FOR SEQ ID NO: 78:

(i) SEQUENCE CHARACTERISTICS:
            (A) LENGTH: 9 bases
            (B) TYPE:  nucleic acid
            (C) STRANDEDNESS: Not Applicable
            (D) TOPOLOGY: linear (ii) MOLECULE TYPE:Genomic DNA (iii) HYPOTHETICAL: yes (xi) SEQUENCE DESCRIPTION: SEQ ID NO: 78:

CTACGTCCT                                                                     9

(2) INFORMATION FOR SEQ ID NO: 79:

(i) SEQUENCE CHARACTERISTICS:
            (A) LENGTH: 75 bases
            (B) TYPE:  nucleic acid
            (C) STRANDEDNESS: Not Applicable
            (D) TOPOLOGY: linear (ii) MOLECULE TYPE:Genomic DNA (iii) HYPOTHETICAL: yes (xi) SEQUENCE DESCRIPTION: SEQ ID NO: 79:

CTAAGTGTGG CGGAACTACG TCCTCTAACA AGAGATGTGG CGGAACTACG TCACGTCCTC      60

TAACAAGAGA GGACT                                                      75

(2) INFORMATION FOR SEQ ID NO: 80:

(i) SEQUENCE CHARACTERISTICS:
        (A) LENGTH: 75 bases
        (B) TYPE: nucleic acid
        (C) STRANDEDNESS: Not Applicable
        (D) TOPOLOGY: linear (ii) MOLECULE TYPE:Genomic DNA (iii) HYPOTHETICAL: yes (xi) SEQUENCE DESCRIPTION: SEQ ID NO: 80:

```
CTAAGTGTGG CGGAACTACG TCACGTCCTC TAACAAGAGA TGTGGCGGAA CTACGTCCTC    60

TAACAAGAGA GGACT                                                    75
```

(2) INFORMATION FOR SEQ ID NO: 81:

(i) SEQUENCE CHARACTERISTICS:
        (A) LENGTH: 22 bases
        (B) TYPE: nucleic acid
        (C) STRANDEDNESS: Not Applicable
        (D) TOPOLOGY: linear (ii) MOLECULE TYPE:Genomic DNA (iii) HYPOTHETICAL: yes (xi) SEQUENCE DESCRIPTION: SEQ ID NO: 81:

```
TGCCAGAAGA GCCAAGGACA GG                                            22
```

(2) INFORMATION FOR SEQ ID NO: 82:

(i) SEQUENCE CHARACTERISTICS:
        (A) LENGTH: 20 bases
        (B) TYPE: nucleic acid
        (C) STRANDEDNESS: Not Applicable
        (D) TOPOLOGY: linear (ii) MOLECULE TYPE:Genomic DNA (iii) HYPOTHETICAL: yes (xi) SEQUENCE DESCRIPTION: SEQ ID NO: 82:

```
TAAGGGTGGG CCCCTAGACC                                               20
```

(2) INFORMATION FOR SEQ ID NO: 83:

(i) SEQUENCE CHARACTERISTICS:
        (A) LENGTH: 20 bases
        (B) TYPE: nucleic acid
        (C) STRANDEDNESS: Not Applicable
        (D) TOPOLOGY: linear (ii) MOLECULE TYPE:Genomic DNA (iii) HYPOTHETICAL: yes (xi) SEQUENCE DESCRIPTION: SEQ ID NO: 83:

```
CATTTGCTTC TGACACAACT                                               20
```

(2) INFORMATION FOR SEQ ID NO: 84:

(i) SEQUENCE CHARACTERISTICS:
        (A) LENGTH: 19 bases
        (B) TYPE: nucleic acid
        (C) STRANDEDNESS: Not Applicable
        (D) TOPOLOGY: linear

```
        (ii) MOLECULE TYPE:Genomic DNA (iii) HYPOTHETICAL: yes (xi) SEQUENCE DESCRIPTION: SEQ ID NO: 84:

TCTCCTTAAA CCTGTCTTG                                                   19

(2) INFORMATION FOR SEQ ID NO: 85:

(i) SEQUENCE CHARACTERISTICS:
             (A) LENGTH: 10 bases
             (B) TYPE:  nucleic acid
             (C) STRANDEDNESS: Not Applicable
             (D) TOPOLOGY: linear (ii) MOLECULE TYPE:Genomic DNA (iii) HYPOTHETICAL: yes (xi) SEQUENCE DESCRIPTION: SEQ ID NO: 85:

CCCTGGGCAG                                                             10

(2) INFORMATION FOR SEQ ID NO: 86:

(i) SEQUENCE CHARACTERISTICS:
             (A) LENGTH: 14 bases
             (B) TYPE:  nucleic acid
             (C) STRANDEDNESS: Not Applicable
             (D) TOPOLOGY: linear (ii) MOLECULE TYPE:Genomic DNA (iii) HYPOTHETICAL: yes (xi) SEQUENCE DESCRIPTION: SEQ ID NO: 86:

GTCTTGTAAC CTTG                                                        14

(2) INFORMATION FOR SEQ ID NO: 87:

(i) SEQUENCE CHARACTERISTICS:
             (A) LENGTH: 10 bases
             (B) TYPE:  nucleic acid
             (C) STRANDEDNESS: Not Applicable
             (D) TOPOLOGY: linear (ii) MOLECULE TYPE:Genomic DNA (iii) HYPOTHETICAL: yes (xi) SEQUENCE DESCRIPTION: SEQ ID NO: 87:

TGATGACTGG                                                             10

(2) INFORMATION FOR SEQ ID NO: 88:

(i) SEQUENCE CHARACTERISTICS:
             (A) LENGTH: 10 bases
             (B) TYPE:  nucleic acid
             (C) STRANDEDNESS: Not Applicable
             (D) TOPOLOGY: linear (ii) MOLECULE TYPE:Genomic DNA (iii) HYPOTHETICAL: yes (xi) SEQUENCE DESCRIPTION: SEQ ID NO: 88:

ATACCAACCT                                                             10
```

USE OF CONTINUOUS/CONTIGUOUS STACKING HYBRIDIZATION AS A DIAGNOSTIC TOOL

This application is a Divisional of a Continuation-in-Part (Ser. No. 08/855,372) filed May 13, 1997, now U.S. Pat. No. 6,090,549 wherein the parent (Ser. No. 08/587,332) filed Jan. 16, 1996, of said CIP has issued as U.S. Pat. No. 5,908,745.

CONTRACTUAL ORIGIN OF THE INVENTION

The United States Government has rights in this invention pursuant to Contract No. W-31-109-ENG-38 between the U.S. Department of Energy and the University of Chicago representing Argonne National Laboratory.

BACKGROUND OF THE INVENTION

1. Field of the Invention

This invention relates to a method for analyzing DNA sequences and more particularly this invention relates to a method for using sequencing by hybridization with oligonucleotides associated with polyacrylamide matrices, including continuous/contiguous stacking hybridization methods, to detect disease-associated alleles.

2. Background of the Invention

Present techniques for determining the existence of disease-associated alleles in patient DNA are complex, inefficient and somewhat time consuming. This is due to the fact that technologies applied to mutation location stem from complex and other error-prone base sequencing procedures. For example, one multi-step DNA sequencing approach, the Maxam and Gilbert method, involves first labeling DNA, and then splitting the DNA with a chemical, designed to alter a specific base, to produce a set of labeled fragments. The process is repeated by cleaving additional DNA with other chemicals specific for altering different bases, to produce additional sets of labeled fragments. The multiple fragment sets then must be run side-by-side in electrophoresis gels to determine base sequences.

Another sequencing method, the dideoxy procedure, based on Sanger, et al. *Proc. Natl. Acad. Sci. USA* 74, 5463–7 (1977) first requires the combination of a chain terminator as a limiting reagent, and then the use of polymerase to generate various length molecules, said molecules later to be compared on a gel. The accompanying lengthy electrophoresis procedures further detracts from the utility of this method as a fast and efficient diagnostic tool.

A more recently developed sequencing strategy involves sequencing by hybridization on oligonucleotide microchips, or matrices, (SHOM) whereby DNA is hybridized with a complete set of oligonucleotides, which are first immobilized at fixed positions on a glass plate or polyacrylamide gel matrix. There are drawbacks to this technique, however. For instance, given that short nucleotide sequences are repeated rather frequently in long DNA molecules, the sequencing of lengthy genome strings is not feasible via SHOM.

Furthermore, the procedures for manufacturing sequencing microchips with the required, large number of immobilized oligonucleotides is not perfected. For example, if immobilized octamers are utilized to determine the positions of each of the four bases in genomic DNA, then $4^8$ or 65,536 such octamers need to be fabricated and subsequently immobilized on the gel. Also, hybridization with short oligonucleotides is affected by hairpin structures in DNA.

Yet another disadvantage in using SHOM is its ineffectiveness in discriminating perfect DNA-oligomer duplexes from mismatched ones, particularly mismatched duplexes at terminal positions. Such terminal mismatches are harder to discriminate than internal mismatches.

In a variation of SHOM, sequencing of DNA strings is facilitated via a contiguous stacking hybridization (CSH) approach, whereby the microchip, comprising a gel embedded with immobilized oligomer such as an octamer (8-mer), is hybridized first with DNA and then with a fluorescently labeled oligomer such as a pentamer (5-mer). The resulting, contiguous 13 base-long oligomer (the 5-mer in a juxtaposed position to the immobilized 8-mer) thus formed acts as a probe to the DNA region.

The efficiency of CSH is due to a more stable probe being formed when the immobilized oligomer is positioned side by side with the mobilized oligomer. This extended complimentary probe therefore results in a more stable duplex between the probe and target DNA.

As with SHOM, however, there are drawbacks with CSH. First, in addition to the 65,536 immobilized oligomers already required to produce the immobilized oligo fraction in the gel matrix (discussed supra), the number of mobile oligomers (i.e. mobile pentamers) necessary to completely read the subject DNA via CSH is also formidable. When mobile pentamers are used, for example, given the possibility of any one of four bases at any one base position on the pentamer, all variations of the pentamer ($4^5$=1,024) must be produced and hybridized with the chip. Furthermore, the microchip, containing the duplexed DNA must be contacted with all the 1,024 pentamers in separate hybridization procedures (i.e. performing 1,024 additional hybridization rounds) to fully sequence the subject DNA.

Hybridization of filter-immobilized DNA with oligonucleotides in solution also has been suggested for mutation detection. However, this approach is too cumbersome for screening all possible base changes in some genes. For example, in the case of β-thalassemia, the number of changes exceeds 100.

A need exists in the art to provide an efficient method for diagnosing disease by detecting multiple mutation sequences in patient DNA. Such a method must incorporate a minimal number of oligonucleotides and utilize a minimal number of hybridization steps. The method also must be of sufficient efficiency so as to effectively discriminate perfect duplexes from imperfect ones.

SUMMARY OF THE INVENTION

It is an object of the present invention to provide a method for detecting multiple DNA base mutations, which are specific for certain diseases, that overcomes the disadvantages of the prior art.

Yet another object of the present invention is to provide a method to sequence target DNA by hybridizing the DNA first to oligonucleotide microchips and then subjecting the resulting DNA-oligo duplex to mobile oligonucleotides. A feature of the invented method is using a minimal number of mobile oligonucleotides to extend the sequences of immobilized nucleotides which are complementary to disease-associated alleles. An advantage of the invented method is enhanced detection of the DNA-oligonucleotide duplex.

Still another object of the present invention is to provide a procedure for more accurately detecting the presence of disease-associated DNA mutations. A feature of the invention is the use of universal bases or a mixture of all four bases in oligonucleotide probe sequences. An advantage of the method is producing a more sensitive method for discriminating perfect duplexes from mis-matched duplexes in SHOM procedures. Another advantage is to increase the efficiency of CSH by reducing the number of mobile oligomers and hybridization rounds.

Another object of the invented method is to provide a procedure, incorporating a minimum number of stacking hybridization steps, that can accurately determine the existence of disease-associated DNA mutations. A feature of the method is the simultaneous hybridization of patient DNA, first duplexed with immobilized DNA, with mobile oligonucleotide probes, each of said probes containing a different fluorochrome. An advantage of the invented method is to decrease the number of hybridization steps, thereby expediting the process of mutation detection.

Yet another object of the present invention is to provide a method for sequencing DNA and RNA molecules with elongated, immobilized probes. A feature of the invention is the ligating together of probes after their juxtaposition to each other on an immobilization substrate. An advantage of the invention is the ability to sequence-test long DNA and RNA molecules containing repeat regions. An additional advantage is the use of the invented method to simplify the sequencing of similar genes and genomes.

Still another object of the present invention is to provide a diagnostic method for detecting disease. A feature of the invention is the covalent extension of probes to a target DNA or RNA molecule. An advantage of the invention is the use of the probes as a diagnostic tool to determine the extent of the existence of repeat sequences in the target molecule, the existence of which is often proportional to severity of disease coded by the molecules.

In brief, the objects and advantages of the present invention are achieved by a method for detecting disease associated alleles in patient genetic material comprising immobilizing a first group of oligonucleotide molecules of a predetermined length on a predetermined position on a substrate, said oligonucleotide molecules synthesized to compliment base sequences of the disease associated alleles; contacting the genetic material with said first group of oligonucleotides to form duplexes; contacting the duplexes with a second group of oligonucleotide molecules, said second group of oligonucleotide molecules synthesized to extend the predetermined length of the oligonucleotide molecules of the first group, and where each of the oligonucleotide molecules of the second group are tagged with a different fluorochrome which radiates light at a predetermined wavelength; washing the contacted the duplexes; and comparing the light patterns radiating from the predetermined positions on the substrate with light patterns of various diseases prepared on identical substrates.

Also provided is a method for determining the length of a repeat base sequence in a target oligonucleotide molecule comprising immobilizing a first end of a starter oligonucleotide molecule; contacting said starter oligonucleotide molecule with the target oligonucleotide molecule so as to cause the target oligonucleotide molecule to hybridize with said starter oligonucleotide molecule; contacting a labeled oligonucleotide extender molecule to the target oligonucleotide molecule; allowing said labeled oligonucleotide extender molecule to hybridize with a region of the target oligonucleotide molecule near a second end of said starter oligonucleotide molecule; determining the base sequence of said region of the target oligonucleotide molecule that is hybridized with said labeled extender molecule; replacing said labeled oligonucleotide extender molecule with an unlabeled oligonucleotide extender molecule having the same base sequence as said labeled oligonucleotide extender molecule; ligating said second end of starter oligonucleotide molecule to said unlabeled oligonucleotide extender molecule so as to create a new starter oligonucleotide molecule hybridized to the target oligonucleotide molecule; and repeating the above steps until a nonrepeating base sequence of the target molecule is detected.

BRIEF DESCRIPTION OF THE DRAWING

The present invention together with the above and other objects and advantages may best be understood from the following detailed description of the embodiment of the invention illustrated in the drawings, wherein:

FIG. 5 is a diagram of fluorograms of specific hybridization experiments using a plurality of tags, in accordance with the present invention;

FIG. 6A is a schematic representation of a target molecule containing repeat sequences subjected to hybridization-ligation processes, in accordance with features of the present invention;

FIG. 6B depicts the stability of various hybrid products stacked with probes illustrated in FIG. 6A;

FIG. 6C depicts the hybridization of target DNA with labeled probes, in accordance with features of the present invention;

FIG. 8. is a schematic depiction of a method for determining the base sequence of an unknown oligo strand using phosphorylation and ligation of oligomer probes, in accordance with the present invention.

DETAILED DESCRIPTION OF THE INVENTION

Figure 1:
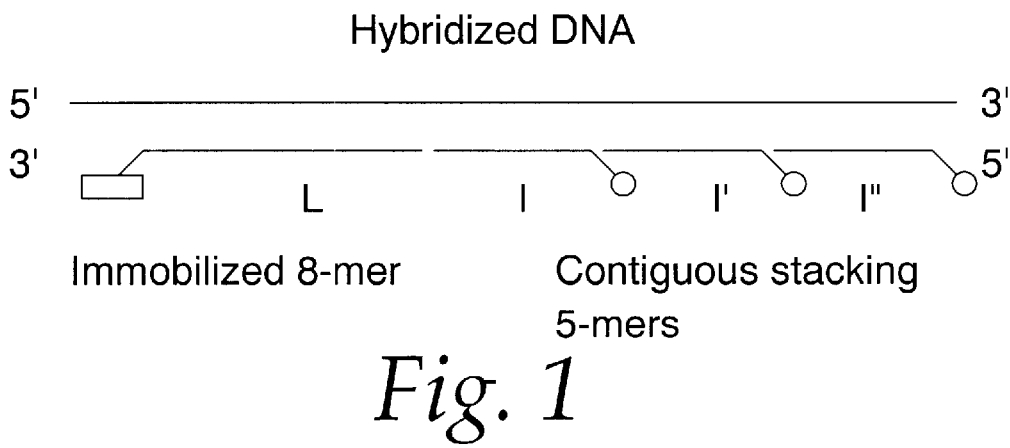
FIG. 1 is a schematic diagram of the stacking between subject matter DNA, gel-immobilized oligonucleotide sequences and oligonucleotide extending sequences, in accordance with the present invention.

A method has been developed to detect DNA mutations associated with specific diseases. The method involves hybridizing patient genetic material, such as DNA or RNA to a plurality of selected nucleotide polymers having predetermined lengths, said polymers complementary to disease-associated alleles. The existence of mutations corresponding to specific diseases are determined by comparing the resulting fluorescence intensity and or patterns with those patterns which are fingerprints for specific diseases.

A preferred method is the immobilization of each of the oligonucleotide molecules in specific array locations on a gel to form microchips. The microchips are then sequentially hybridized, with the fragment of DNA (for example PCR product or clone) from an established disease-associated, allele-containing genome, and then with mobile-phase oligonucleotides that are labeled. Each of said mobile oligonucleotides may contain different fluorohromes. After reading the fluorescent pattern, the chip is washed and then subjected to a sample derived from genomic DNA (i.e. patient provided) and the same fluorescently labeled mobile phase oligonucleotides. The now-contiguous oligomeric complex thus forms a probe to aberrant DNA regions or mutations. Hybridization patterns are then compared to determine the existence of mutations.

An adjunct to the above-described contiguous stacking method involves extending the length of only those immobilized oligonucleotides that are involved in hybridization to thereby increase the sequence efficiency of the microchip. The inventors have elucidated a protocol for the site specific phosphorylation and ligation of gel-immobilized oligonucleotides. The combined use of contiguous stacking hybridization, phosphorylation and ligation has resulted in an increased reliability of sequence measurements and the ability to scrutinize longer-length DNA or RNA.

The above-mentioned phosphorylation and ligation technique is particularly valuable in sequencing long DNA containing internal repeats, and therefore identifying unique sequences that flank such repeats. Measurements of the number of these repeats is an important task since changes in the repeat length in some genes can cause genetically predisposed diseases. The method, in combination with DNA and RNA fractionation techniques also developed by the inventors, is also valuable for sequence comparison of homologous genomic regions without intermediate mapping and cloning.

The invented method obviates the need for the fabrication and array placement of large numbers of immobilized oligomers. Instead, the invented protocol involves the manufacture of microchips that contain a selection of specific synthetic oligomers, having a length of between approximately 6 and 16 bases, that are immobilized on a gel. Instead of the 65,536 immobilized octamers needed to detect every base sequence in an 8-base probe, relatively fewer oligomers, from between approximately a few dozen to a few hundred, that are specific for disease-associated allele sequences, are required, depending on the number of fingerprint mutations previously noted in the aberrant gene responsible for the disease. For example, a microchip with two hundred octamers, which are manufactured to complement a known allele sequence, and which are also manufactured to partly overlap each other by three nucleotides, is utilized to cover a one thousand nucleotide-long DNA molecule, by increments of five. Patient DNA is hybridized with the microchip to localize the pentanucleotide region having a changed structure. Then, successive rounds of hybridization with labeled pentamers, corresponding to the mutations, are utilized to identify the mutation.

FIG. 1 illustrates one embodiment of the invented stacking method. As depicted therein, an immobilized oligonucleotide of length L is hybridized with a DNA fragment. When additional oligonucleotides of length l, l' and l" are added, the duplexes formed between all of the pentamers and the DNA are stronger together than if taken separately, particularly when there is a contiguous (uninterrupted) stacking interaction between L, l, l' and l".

The inventors have found that the effective CSH interaction lengths of a microchip with immobilized octamers hybridized with one, two or three pentamers range from between 13 bases and 23 bases. Generally, a chip containing immobilized octamers is hybridized with a solution of target DNA. This is followed by several rounds of successive hybridizations with fluorescently-labeled pentamers. Thus, after the target DNA hybridizes first to the immobilized octamer, the same DNA will be available to form a duplex with one or more of the pentamers in the successive hybridization steps. Hybridization of each oligomer is detected by the fluorescence emission of the particular fluorochrome that is coupled to any one oligomer probe.

Figure 2:
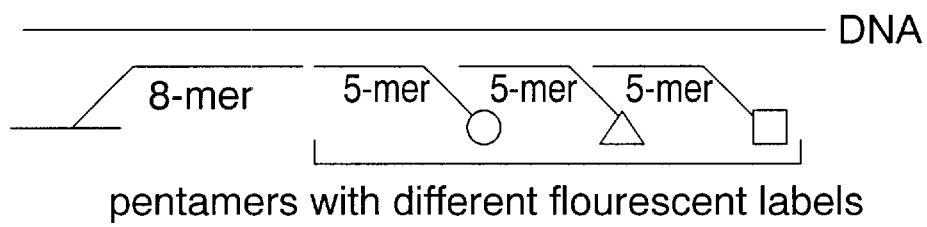
FIG. 2 is a schematic diagram of the stacking between subject matter DNA, gel-immobilized oligonucleotide sequences and a plurality of mobile oligonucleotide sequences, each mobile sequence containing a different dye, in accordance with the present invention.

In another embodiment, depicted in FIG. 2, oligonucleotides l, l' and l" are labelled with different fluorescent dyes. This allows discrimination between duplexes having lengths of for example, 8 nucleotides, 13 nucleotides, 18 nucleotides or 23 nucleotides, when immobilized oligomer fractions are 8 nucleotides long and the mobile oligomer fractions are 5 nucleotides, or multiples of 5 nucleotides long. The use of different fluorescent markers allows for simultaneous hybridization of different mobile fractions, thereby reducing the number of hybridization steps.

The invented CSH method is also applied to identify unknown base changes. In one instance, this can be accomplished if the complete set of all possible 1024 mobile pentamers is available, for example, in fragments 1,000 bases long. The first hybridization is conducted with the 200 overlapping immobilized oligomers, as discussed supra, to pin-point the region where DNA changes exist. Then, hybridization with the 1,024 mobile pentamers is conducted.

Furthermore, fewer than 1,024 hybridization steps are possible with the invented method. For example, the number of hybridization steps is decreased by a factor of four, to 256 steps (i.e. $4^4=256$), when mobile pentamers, which vary from each other in just one base position, are used.

When pentamers containing four universal bases and only one base are used, the number of hybridization steps are decreased to 20. For example, complementarity of the mobile oligomer components to the hybridized DNA is imparted by their incorporation of universal bases, such as 5-nitroindole, 3-nitropyrrole,inosine, or all four bases (the four bases being those found in DNA, namely guanine, cytosine, thymine, and adenine). As a result, successive treatment of the microchip with all possible sequences of the mobile fraction (1024 in the case of a pentamer) is obviated. As an example, for the detection of T-based localization in the DNA fragment, only five successive rounds of hybridization need be performed with pentamers of the following structure:

(first round) A-N-N-N-N-fluorochrome A;

(second round) N-A-N-N-N-fluorochrome A;

(third round) N-N-A-N-N-fluorochrome A;

(fourth round) N-N-N-A-N-fluorochrome A;and (fifth round) N-N-N-N-A-fluorochrome A;

where N designates the universal base (i.e., the four bases A,G,T, and C) and wherein each pentamer is labelled with the same chromophore. With all four bases to be analyzed, only 20 rounds of hybridization, instead of 1024, need to be performed.

The use of four different labels decreases the number of necessary hybridization four times more so that only 5 hybridization rounds need to be performed. In this case, at the first round of hybridization, a mixture of four probes is used with the following structure:

A-N-N-N-N-fluorochrome A;

T-N-N-N-N-fluorochrome B;

C-N-N-N-N-fluorochrome C; and

G-N-N-N-N-fluorochrome D.

The color of the resulting spot discloses the substituted base.

To detect the next base, hybridization occurs with another mixture of 5-mers, as follows:

N-A-N-N-N-fluorochrome A;

N-T-N-N-N-fluorochrome B;

N-C-N-N-N-fluorochrome C; and

N-G-N-N-N-fluorochrome D.

Figure 3:
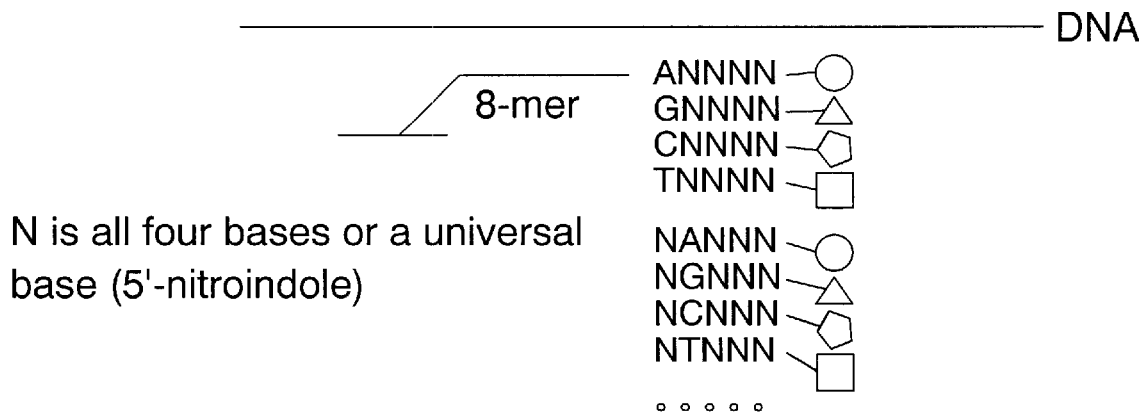
FIG. 3 is a schematic diagram of the stacking between subject matter DNA, gel-immobilized oligonucleotide sequences, and oligonucleotide extending sequences containing universal bases, or a mixture of all four bases, and different fluorochromes, in accordance with the present invention.

The third probe has an ATCG sequence at the third position, the fourth probe has an ATCG sequence at the fourth position, and the fifth probe has an ATCG sequence at the fifth position. This scenario is depicted in FIG. 3.

In addition to the use of universal base or four-base approach, different mobile oligonucleotides, among the 1024 possibilities in the case of a pentamer mobile fraction, can be labeled with different fluorochromes. In the case of two different labels, the number of hybridizations will decrease by a factor of two. In the case of four different labels, the number of required hybridizations will decrease by a factor of four. This use of different labels is illustrated in FIGS. 2 and 3 whereby the geometric shapes of a circle, triangle, pentagon and square graphically represent different tags or fluorochromes.

The resulting hybridization of genomic DNAs and pentamers to the microchips are detected using a multi-wave length fluorescence microscope coupled to a CCD-camera. Identification of the alleles present in the patient genomic DNAs are then determined by analysis of the hybridization patterns.

Microchip Manufacturing Detail

Suitable immobilization substrates must have high capacity, be relatively rigid and durable, and should be benign viz hybridization. The use of gel-support for oligonucleotide immobilization offers many advantages. Oligonucleotides are tethered into the gel volume instead of being attached to the surface, thereby providing for one hundred times the capacity for immobilization (about 1 nmole/mm$^2$) than glass.

A matrix of polyacrylamide gel-elements is prepared by first polymerizing a 10–30 $\mu$m gel-layer on a glass surface. A myriad of techniques are available, including that disclosed by K. R. Khrapko et al. *J. DNA Sequencing and Mapping* Vol 1, pp. 375–388, and incorporated herein by reference.

Strips of gel are then removed in perpendicular directions to yield gel squares. Each square is isolated from adjacent squares by strips of naked glass, said strips wide enough to prevent accidental mixing of oligomers. The inventors have found that widths of between approximately 80 $\mu$m and 200 $\mu$m provide good results. A scribing machine facilitates this removal, but photolithography methods are also applicable for the preparation of such gel-square elements. A laser method, developed by the inventors and disclosed in PCT/RU 92/00052, 1992, incorporated herein by reference, is also suitable.

Gel-element sizes range from approximately 40 $\mu$m×40 $\mu$m×20 $\mu$m for a micro-chip to 1 mm×1 mm×30 $\mu$m for macro-chips. Generally, chip sizes ranging from 20 $\mu$m×20 $\mu$m×20 $\mu$m to 1 mm×1 mm×30 $\mu$m produce good results. In as much as polyacrylamide gels have low fluorescent background, the sensitivity of the measurements (i.e., the ratio of signal to background) will increase with miniaturization of the gel-cell sizes, resulting in an increase in density of the DNA-oligonucleotide duplexes. The inventors were able to detect fluorescence down to 10 amol of labeled target per 100 $\mu$m×100 $\mu$m.

Oligonucleotide Synthesis Detail

The synthesis of oligonucleotides for immobilization started from 3-methyluridine, located at the 3'-end, as described in Krapko, noted supra. Oligonucleotides for hybridization were labeled with TMR either at the 3'-end by terminal transferase, provided by Promega (Madison, Wis.) and fluorescently labeled dUTP. Alternatively the 5' amino-group was labeled with an excess of N-hydroxysuccinimide ester of 5-carboxytetramethylrhodamine (Molecular Probe, Inc. Eugene, Oregon) in DMSO with 50 mM sodium borate buffer, pH 9.0 at 60° C. for 30 minutes. The labeled oligonucleotides were further purified by PAGE and recovered as described in J. L. Mergny et al. *Nucleic Acid. Res.* 2 2, 920–928.

The synthesis of oligonucleotides containing universal bases is to similar.

Oligonucleotides containing the 3-methyluridine at the 3' end were effective couplers through the aldehyde groups formed after oxidation of the 3-terminal ribose residues with sodium periodate. Prior to transfer to the gel, up to 2 nmol of oligonucleotide solution is initially oxidized in 1 mM to 10 mM NaIO$_4$ at room temperature for 10–100 minutes. Then, ethylene glycol was added to a final concentration of 50 mM. Oligonucleotides were lyophilized, dissolved in water, and then used for spotting, or alternatively, stored in the wells, 2 mm in diameter, of the teflon microliter plate, where the oxidation was initially carried out. Attachment occurs between the oxidized 3' terminal residue of the oligo and the hydrazide groups of partially modified polyacrylamide gel, whereby the gel was first activated by substituting some amide groups for hydrazide ones.

The 3-methyluridine is a good anchor in as much as it forms no stable base pairs with subject DNA.

Oligonucleotide was applied by robot onto the gel-elements in aliquots of 1 nanoliter ($10^{-9}$ liter) or more. The application technique uses a thin thermostabilised metal pin with a hydrophobic side surface and a hydrophilic end-face which determines the spotting volume. Pin temperature is kept close to the dew point to avoid evaporation of the water solution containing the oligonucleotides.

This transfer technique, developed by the applicants, is more fully disclosed in PCT/RU #94/000180, incorporated herein by reference.

Once the micro-volumes of the solutions of the bioorganic compounds (the oligomers) have been applied to all cells of the matrix, the micro-matrix temperature is set equal to or below the dew point of the ambient air. The temperature is maintained until swelling of the gel is complete and non-coalescent droplets of water-condensate appear in the spacings between the cells. Then, a thin layer of an inert non-luminescent oil (such as NUJOR Mineral Oil from Plough, Inc.) is cautiously applied to the micro-matrix surface, the thickness of the latter layer being over 100 $\mu$m. The micro-matrix is kept under the oil layer until the immobilization process is complete, preferably for at least 48 hours. The oil is then removed with a solvent, such as ethanol and water, and the matrix is dried and stored ready-for-use. More elaborate discussion of the foregoing matrix preparation procedure is found in PCT/RU94/00178, incorporated herein by reference.

The bond between an oligonucleotide and polyacrylamide is stabile enough for the matrix to withstand 10–15 rounds of hybridization without any noticeable degradation. The half-life of the oligonucleotide-gel bond at 60° C. is 2 hours, and at 25° C., 36 hours.

Oligonucleotides are immobilized on the gel in spaced arrays so as to prevent interference during hybridization and enhanced hybridization efficiencies. Gel-loading capacity limits of between 0.01 percent and 30 percent yield good results, with a preferable range of between approximately 0.1 percent and 10 percent. Concentrations of the oligo to the subject DNA can vary, and generally range from between 100 to 1,000 times higher in concentration compared to the subject DNA. Convenient subject DNA concentrations range from 0.1 to 1 picomole (pmole=$10^{-12}$ moles) in one microliter, and a typical oligo concentration is 100 micromoles (fmole=$10^{-15}$ moles) per gel element of 100 square centimeters.

It was observed that more than 70 percent of gel-immobilized oligonucleotides formed duplexes with DNA. The effective temperature stability of duplexes formed between DNA and gel-immobilized oligonucleotides depend on their concentrations and base-pair lengths. Generally, the inventors obtain good DNA complexing with immobilized oligomers at temperatures ranging from between approximately 0° C. and 60° C. Duplexing is further enhanced at high temperatures when oligonucleotides with relatively long base-pair lengths (e.g. 10-mers and 12-mers) are used. For example, when using immobilized pentamers, good duplexing occurs at between 10° C. and 20° C. When using immobilized octamers, preferable temperatures are selected from a range of between approximately 25° C. to 45° C. across the 0.01 percent to 30 percent gel capacity spectrum. This flexibility in gel loading provides the ability to equalize the stability of AT- and GC-rich duplexes in instances where universal bases are not used but where a plurality of different fluorochromes are utilized.

The inventors have found that the incorporation of additional universal bases in the mobile oligomer fraction stabilizes pentamers. Essentially, the incorporation of said universal bases turns terminal mismatches into internal mismatches, which are more easily discriminated from perfect duplex images.

Hybridization, Washing and Staining Detail

All procedures were performed on a Peltie thermotable. Hybridization of a microchip with fluorescently labeled DNA was carried out at 0° C. for 30 minutes in 1 μl of washing buffer with 1 percent TWEEN 20 (Calbiochem, La Jolla, Calif.) detergent or any other detergent, specifically a detergent containing polyoxyethylenes. Washing buffer contained 1 M NaCl, 5 mM Na phosphate (pH 7.0), 1 mM EDTA. Thereafter 100 μl of washing buffer was pipetted on the microchip at 0° C. for 10 seconds and carefully pipetted off to remove unhybridized DNA. The washing could be repeated by varying the temperature and duration.

Contiguous stacking hybridization is carried out by hybridizing the microchip with 1 μmole of unlabeled target at 0° C. for 30 minutes, and optionally, washed at 15° C. for 2 minutes, as described, supra. The second round of hybridization was carried out with 1 μl mixture of fluorescently labeled 5-mers (5 pmol each) at 0° C. for 10 minutes. The matrix was rinsed once with washing buffer with 1 percent TWEEN 20. While a washing step is not usually necessary, any washing procedures employed usually encompassed washing off the hybridized 5-mers at 15° C. for 2 minutes, and hybridization with the other mixtures of 5-mers was repeated under the same conditions.

Fluorescence Analysis Detail

A multi-wave length fluorescence microscope coupled with a CCD-camera was assembled for image analysis. An objective yielding a 3-mm observation field enabled the simultaneous analysis of over 1,000 elements of the microchip at once. Specifically, the microscope (350 W high pressure mercury lamp, Ploem opaque with interference excitation and barrier filters for TMR) equipped with special optics and a CCD camera was built. The 3×objective with the 0.4 numerical aperture allows the illumination of the object field up to 7 mm in diameter and project 2.7×2.7 mm of the microchip on the CCD matrix. The CCD head is similar to that manufactured by Princeton Instruments (Trenton, N.J.). The exposure time varied from 0.4 to 30 seconds with a readout time of about 1.3 seconds. Variation in the sensitivity within the object area did not exceed 5 percent. The system allows operation with 1.7×objective with the same numerical aperture for analyzing 5×5 microchip areas. The instant configuration allows for rapid change-out of Filters for different fluorochromes.

The image of the microchip on the CCD camera was accommodated by a microcomputer, similar to the configuration disclosed in Khrapko, K. R. et al. *J. DNA Sequencing and Mapping*, 1, pp. 375–388, and incorporated herein by reference. For printing, linear transformation was used. This brought the highest pixel values to the same level for all images. For digital estimation, the image of the microchip element was fully covered by a 'square' twice the size of the element. Then a frame was constructed around the 'square' with equal square area. The signal of the element was calculated as the signal from the square minus the signal from the frame.

Fluorochrome Detail

Tetramethylrodamine (TMR) was used as a dye for labeling either the DNA or the mobile oligomers. Other dyes that are suitable labeling compounds include, but are not limited to, fluoresceine, Texas Red, Cascade Blue, and rhodamine, all available from Molecular Probes. HEX™, marketed by Applied Biosystems in Foster City, Calif., is another suitable dye. In the case of DNA-labeling, before measurements the microchip is incubated with fluorescent tagged DNA at 0° C. for 30 minutes and then rinsed for 10 seconds with washing buffer to remove unbound targets. Perfect duplexes are discriminated already in the process of hybridization despite rather high intensities of the fluorescence signal from the unbound target. More effective discrimination of perfect duplexes from mismatched ones are achieved by plotting the dissociation curve either at temperature gradient or at a fixed temperature while changing the duration of washing. Real-time measurements allowed for the choice of optimal conditions for discrimination when the mismatched signals are close to background levels. Temperatures are controlled by a Peltie thermotable.

PCR Detail

PCR amplifications were performed by an adapted procedure by Postnikov et al. *Hemoglobin* 1 7,439–453 (1993), and incorporated herein by reference. Initially, amplification of 421 bp-long product was carried out with 1 ng of genomic DNA, primers #12005 TGCCAGAAGAGCCAAGGA-CAGG (SEQ. ID. No:81) and #12406 TMGGGTGGGCCCCTAGACC, (SEQ. ID. No:81) The reaction conditions were as follows: 30 cycles with 40 seconds at 93° C., 30 seconds at 67° C. and 30 seconds at 72° C. 5 μl of the PCR were transferred to the reaction mixture for amplification with nested primers. Nested primers, #12156 ATUTGCTTCTGACACAACT (SEQ. ID. No:83) and #12313 TCTCCTTAAACCTGTCTTG, (SEQ. ID. No:84) were used to amplify 176 bp-long DNA for 25 cycles (30 seconds at 90° C., 30 seconds at 50° C., 20 seconds at 72° C.). The PCR with fluorescently nested primers (labeled #12272 CCCTGGGCAG (SEQ. ID. No:85) and normal #12299 GTCTTGTAACCTTG) (SEQ. ID. No:86) was carried out for 25 cycles (30 seconds at 80° C., 30 seconds at 35° C.) and yielded 32 bp product. PCT was purified by PAGE or by enrichment procedures.

EXAMPLE 1

Figure 4:
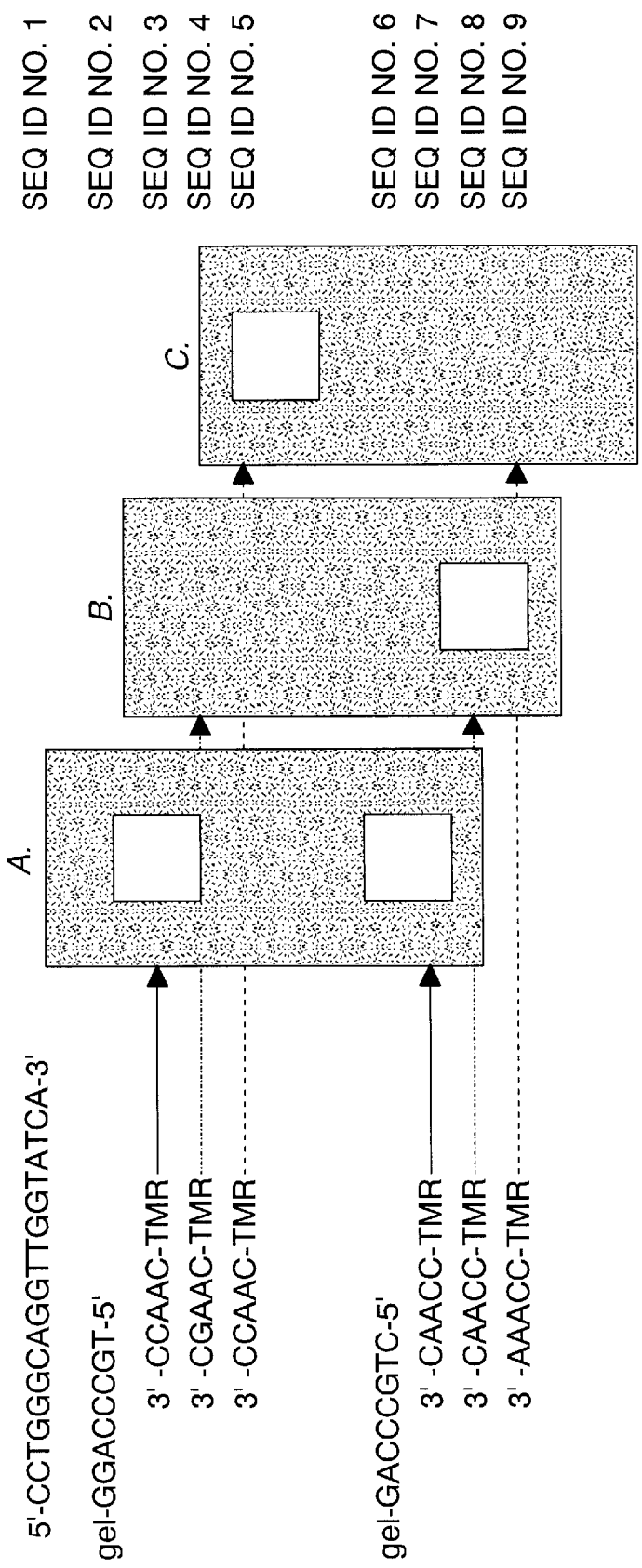
FIG. 4 is a diagram of fluorograms of specific hybridization experiments with specific immobile and mobile oligonucleotides, in accordance with the present invention.

Two 8-mers located one and two bases away from a mutation site were immobilized on a microchip, and the microchip was hybridized to the unlabeled 19-mer. Then the duplexes formed on the microchip were hybridized in three more rounds with pools of two labeled 5-mers. The results are illustrated in FIG. 4. Some hybridized pentamers formed perfect duplexes in a juxtaposed position to the immobilized 8-rner and extended it to a 13 bp-long duplex. These 13-base perfect duplexes were stable due to stacking interactions between 5'- and 3' terminal bases of the 8-iner and 5-iner, respectively, despite lacking a phosphodiester bond. Mismatches in the internal, or even in the terminal, position destabilized the interaction of the 5-mers much more than 8-mers.

As can be noted in FIG. 4, the mismatched 5-mers were either not hybridized at all or washed out at much lower temperature than fully complementary 5-mer. Therefore, inclusion of 5-mers provided better discrimination of perfect duplexes from mismatched ones than just immobilized 8-mers, particularly in the case of terminal mismatches. The 8-mer duplexes remained stable under the washing conditions for the pentamers. The microchips sustained up to 10 rounds of successive hybridization with 5-mers. The 5-mers can also be ligated to 8-mers enzymatically. However, the ligation could complicate those experiments where several rounds of CSH are to be performed.

EXAMPLE 2

FIG. 5 depicts another embodiment wherein a plurality of tags or fluorochromes are used to detect target sequences. In this embodiment, a microchip was constructed, consisting of 10 immobilized octamers, with sequences engineered to affect a three-base overlap. For octamer sequence strings labeled "1.", "2.", and "3.", the sequences varied by either a cytosine or thymine, as indicated by the underscore.

The microchip was hybridized with a 21-nucleotide-containing sequence (21-mer). After the hybridization procedure, unhybridized 21-mer was removed and the microchip was hybridized with a mixture of HEX-labeled pentamer ACCTT and FAM-labeled pentamer GATAC, at a labelling concentration of 50 percent of total pentamer.

Detection of the HEX- and FAM-tags (designated as * and Λ, respectively) was performed by changing to the corresponding sets of optical filters.

The octanucleotide labeled as "−1." was constructed as a negative control, in as much as this string did not interact with a pentamer. Octamer "+1" was constructed as a positive control for hybridization, and for proper filter function.

As can be noted in FIG. 5, the invented contiguous stacking method of using a plurality of tags provides excellent detection of target sequences, and with no false negatives or positives. For example, String "1.", depicting an immobilized octamer stacked with two mobile, and differently-labeled pentamers (in italics), clearly revealed the presence of the target sequence when each tag was utilized.

Hybridization-Lioation Detail

In one exemplary embodiment, discussed infra, a decamer (10-mer) flanking five repeats from the 3' end, is first immobilized onto a gel element. The 10-mer is hybridized with a target ssDNA and then successively ligated with four different unlabeled phosphorylated pentamers (5-mers). Each step of the ligation is controlled by hybridization with fluorescently labeled 5-mers. Lastly, a resulting multi-oligomer probe (a 30-mer in the case when four different pentamers are ligated to the already immobilized decamer) is hybridized with a 5' labeled pentamer to establish repeat length.

Alternatively, only one oligonucleotide can be used for hybridization-ligation walking if its length is a multiple of repeat lengths. For example, a hexamer could be employed for dinucleotide and trinucleotide repeats; a tetramer or octamer can be used for tetranucleotide repeats. Unphosphorylated oligonucleotide and enzymatic phosphorylation are introduced at each walking step to avoid simultaneous coligation of several copies of the oligonucleotide. After the first step of hybridization with DNA, and the second step of ligation of phosphorylated immobilized oligonucleotide with the unphosphorylated repeat oligomers, the ligated product is phosphorylated to carry out the next hybridization-ligation step. This process is suitable in measuring the length of DNA containing tens and hundreds of short repeats, with the 10–50 base pair long blocks of these repeats being used at each step of the hybridization-ligation "walking" procedure.

EXAMPLE 3

Hybridization-Ligation ssDNA containing five tetranucleotide 3'-ACAT-5' repeats was used as a test model. Successive hybridization-ligation "walking" of five pentamers P1–P5 (5-mers) along this ssDNA, first hybridized to an immobilized decamer (10-mer), was performed to measure the repeat length.

As a first step, the decamer was immobilized in each of four gel elements. The decamer-loaded gel element was subsequently hybridized with unlabeled DNA and then contacted with a first fluorescently labeled pentamer. Stability of the first pentamer is enhanced by stacking interactions of adjacent bases at the terminal positions of the first pentamer and the decamer. Other pentamers, which form gaps with the decamer at this particular point of the hybridization sequence are not hybridized due to the lack if stabilizing stacking interactions.

The first labeled pentamer is then washed off the gel element and replaced with an identical pentamer lacking the label. This unlabeled pentamer is ligated to the gel-immobilized decamer (previously phosphorylated), resulting in a 15-mer polymer probe being formed.

In a second round of "walking", a second fluorescently labeled pentamer is hybridized with the DNA at the 5' end of the formed 15-mer. After hybridization, the second labeled pentamer is removed and replaced with a second unlabeled pentamer. This second unlabeled pentamer is then ligated to the 15-mer polymer to form a 20-mer polymer. Two more rounds of hybridization and ligation "walking" extends the length of the micro-chip immobilized polymer to 25 and 30 base lengths, respectively.

The final hybridization of the microchip containing the 30-mer immobilized polymer is carried out with DNA and a fifth labeled pentamer that is complementary to the 3' flanking sequence of the repeat region. This results in the determination that the length of the tetranucleotide repeat in the target DNA is 20 bases (4×5=20).

FIG. 6 provides a schematic view of the repeat length determining process. FIG. 6A shows the results of hybridization-ligation of ssDNA containing five tetranucleotide 3'-ACAT-5' repeats. The successive hybridization-ligation "walking" of five pentamers (P1=5'-GTATG-3', P2=5'-TGTAT-3', P3=5'-ATGTA-3', P4=5'-TATGT-3' and P5=5'-AATTG-3') along the ssDNA, first hybridized to a chip-bonded 10-mer, was carried out to measure the number of repeats. The decamer (5'-TGATGACTGG-3') (SEQ. ID. NO.87) complementary to the ss DNA was immobilized in four adjacent gel pads of the chip, as depicted in FIG. 6C.

The chip, as depicted in FIG. 6C(1) was first hybridized with unlabeled DNA and the fluorescently labeled 5-mer P1. As can be noted in FIG. 6B, column P0 (P0 which denotes hybridization but no ligation) P1 and the decamer formed a stable contiguous 15 basepair duplex with the DNA. P1 was stabilized in the duplex by the stacking interactions of adjacent bases at the terminal positions of P1 and the decamer. As can be noted traveling down the P0 column, the other pentamers (P2, P3, P4, and P5) are not prone to hybridization due to lack of stabilizing stacking interactions.

All of the labeled pentamers were washed off the chip and the unlabeled pentamer P1 was added and ligated to the decamer to create a complementary 15-mer immobilized fraction that is complementary to the DNA. To this 15-mer (depicted in column P1) was added labeled pentamer P2, resulting in an AU intensity of 70 for P2. However, due to incomplete ligation in the previous cycle, a fluorescence intensity of 51 AU (arbitrary units) for P1 was also observed.

As in the previous step, the labeled P2 was washed from the chip and unlabeled P2 was ligated to the existing 15-mer to form a 20-mer immobilized fraction. When labeled P3 was added to the 20-mer, an intensity of 45 was observed (see column+P2). Two additional cycles of hybridization and ligation "walking" with P3 and P4 resulted in elongating the 20-mer to a 25-mer and a 30-mer immobilized oligo. Final hybridization of the 30-mers formed after the four ligations was carried out with P5 which is not complementary to the repeat sequence in the DNA. Therefore, this final hybridization determines the sequence which flanks the 3' end of the repeat region of the DNA while also determining the length of the tetranucleotide repeat as 4×5=20 bases.

Site-directed Phosphorylation and Ligation of Immobilized Oligomers

Figure 7A:
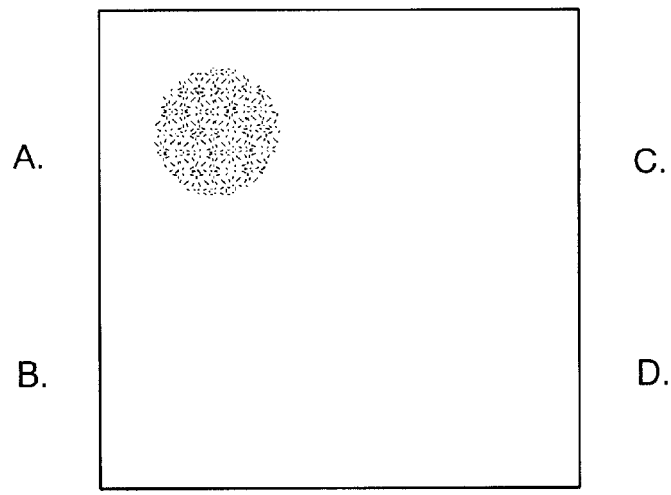
FIGS. 7A, 7B and 7C are radioautographs and fluorographs depicting the efficiencies of the invented phosphorylation and ligation method, in accordance with the invented method.
Figure 7B:
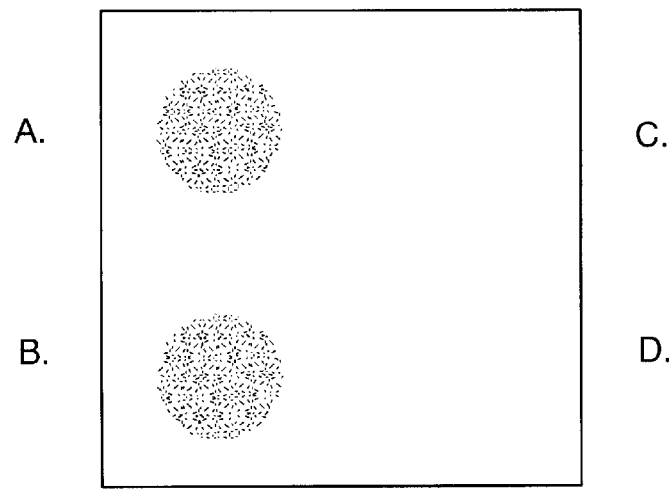
Figure 7C:
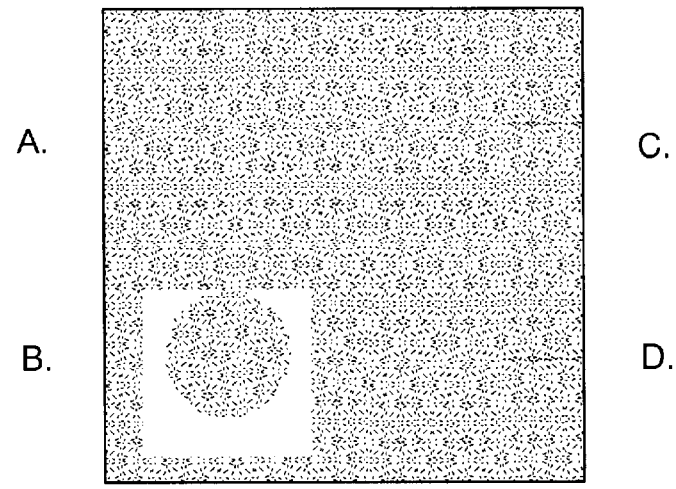

The results of site-directed phosphorylation and ligation on specified pads of a gel pad are shown in FIG. 7. T4 polynucleotide kinase (140 kDa) and T4 DNA ligase (54 kDa) diffused into the four percent polyacrylamide gel of the microchip pads to catalyze phosphorylation and ligation of immobilized oligonucleotides. A $^{32}$P-labeled decamer was immobilized within element "A" and the same nonphosphorylated decamer was attached to the "B", "C" and "D" pads of the array depicted in 7A.

The mixture of the kinase and γ-$^{32}$P-ATP in a buffer was added only to element "B". The same solutions, but lacking kinase, were added to the "C" element to establish a control. After incubation of the array at 37° C. for 3 hours, the $^{32}$p label appeared only in element "B". That no crosstalking of element "B" with "C" or "D" was observed confirms that the invention provides for efficient and site-directed phosphorylation of gel-immobilized oligonucleotides.

Complementary 21 base-long DNA, fluorescently labeled pentamer and DNA ligase were added to the immobilized, phosphorylated decamers (element "B") and immobilized, nonphosphorylated decamers (element "C"). The same solution, but not containing ligase, was added to control elements "A" and "D" containing phosphorylated and nonphosphorylated decamers. After completion of ligation at 4° C. for 5 hours and subsequent washing, the fluorescence label was observed only in element "B", as depicted in FIG. 6c. The results of the ligation experiments substantiated the invented protocol providing for immobilized oligonucleotide phosphorylation and ligation in predefined areas of an oligonucleotide microchip.

A more detailed description of the phosphorylation and ligation protocol, including the production of controls is as follows: Fifty picomoles of synthetic oligodeoxyribonucleotide (5'-ATACCAACCT-r$^{3m}$U-3') (SEQ. ID. NO. 88) was phosphorylated within 10 microliters ($\mu$l) of a reaction mixture containing 1×PNkinase buffer (available from Epicentre Technologies, Madison, Wis.), 15 $\mu$Ci [γ-$^{32}$P] ATP, 500 pmol ATP and 0.5 U T4 Polynucleotide kinase (also from Epicentre Technologies) at 37° C. for 60 minutes. The $^{32}$P-labeled decamer was purified from unincorporated label with Bio-Spin 6 Chromatography Column (Bio-Rad Laboratories, Hercules, Calif.) and immobilized within the "A" gel element of FIG. 6a. The same oligomer, but not phosphorylated, was immobilized within the "B", "C" and "D" pads of the chip depicted in FIG. 6a. Immobilization was carried out at 20° C. for 12 hours. The chip was washed with washing buffer comprising 0.2 M NaCl, 0.2 mM EDTA, 2 mM sodium phosphate, pH 6.8 at 37° C. for one hour and then rinsed with water. The chip was dried and radioautographed with Kodak Scientific Imaging Film X-OMAT.

One microliter of the phosphorylation mixture 1.5 $\mu$Ci [γ-$^{32}$P] ATP, 50 pmol ATP and 0.05 U T4 Polynucleotide kinase in 1×PNkinase buffer was added to gel element "B". As a control, either the same mixture (excluding kinase) was added to pad "C" or 1 $\mu$l of 1×PNkinase buffer was added to gel cell "A". Enzymatic phosphorylation was carried out at 37° C. for 3 hours at 100 humidity. The chip was washed first with washing buffer (0.2. M NaCl, 0.2 mM EDTA, 2 mM sodium phosphate pH 6.8) at 37° C. for 1 hour, then with water, dried and radioautographed. 2.5 $\mu$l of ligation mixture containing 10 pmol of ss DNA (5'-TGGGCAGGTTGGTATCAAGGT-3') complementary to the immobilized decamer, 50 picomol of fluorescently labeled pentamer (5'-HEX-CCTTG-3') stacked to the immobilized decamer, 1 mM ATP, and 0.1 U T4 DNA ligase (from Epicentre Technologies) in 1×T4 DNA ligase buffer (also from Epicentre) were each added to the "B" and "C" gel pads. As a control, 2.5 $\mu$l of the same mixture, excluding ligase, was added to the "A" and "D" gel elements. Ligation was carried out at 4° C. for 5 hours, then the chip was washed with washing buffer (0.2 M NaCl, 0.2 mM EDTA, 2 mM sodium phosphate, pH 6.8) at 10° C. for 5 minutes.

Four pentamers, a decamer and single stranded DNA were synthesized. Also synthesized were the same four pentamers and a fifth pentamer, all five of which contained fluorescein at their 5' end.

One picomole of the decamer and 40 picomoles of each of the first four pentamors were phosphorylated separately with 10-fold excess of ATP and 1 U of T4 Polynucleotide kinase. The phosphorylated decamer was immobilized within four gel pads (100 fmol per 100×100×20 $\mu$m pad) on a micromatrix. Four rounds of successive contiguous stacking hybridization (CSH) followed by ligation were carried out under similar conditions.

The first hybridization was carried out in 10 $\mu$l of hybridization buffer containing 1 $\mu$M fluorescently-labelled first pentamer and 1 $\mu$M of complementary ssDNA. Approximately 10 ml of the hybridization solution was placed on the microchip, and the chip covered with a cover-glass slide over 0.1 mm-thick spacers to be incubated for 5 minutes at 7° C. After the hybridization, the cover glass was removed and the microchip was washed with distilled water for 10 minutes at 37° C. to remove all labelled pentamer. Four microliters of ligation mixture containing 4 pmole of the ssDNA, 40 pmole of the first phosphorylated pentamer, and 1 U T4 DNA ligase in 05.×dilution and 1×ligation buffer (available in the Rapid DNA Ligation Kit from Boehringer Mannheim (Indianapolis, Ind.) were placed on the microchip. Ligation was carried out at room temperature for 4 hours at 100 percent humidity. After completing the reaction, the chip was washed for 10 minutes at 37° C. with distilled water and dried. The next three rounds of hybridization-ligation were carried out with a second pentamer, then a third, and finally a fourth pentamer. Lastly, the ligated 30-mer of the microchip was hybridized with DNA and the labeled fifth pentamer.

Sequencing of Long DNA/RNA Molecules

Aside from determining the length of repeat sections of DNA or RNA molecules, determining the sequence of unknown DNA or RNA molecules also is a high priority. Sequencing efforts using gelmatrices have been relegated to the sequencing of strands of approximately 200 bases in length. This is due to the fact that each cell in a gel matrix must contain only one oligomer. While sequencing sensitivity is proportional to oligomer length, an increase in oligomer length also requires more cells per gel matrix. For example, the use of immobilized hexamers requires that 4096 cells ($4^6$) be constructed, each to hold just one possible hexamer sequence. If octamers are used, then 65, 336 ($4^8$) cells are required.

The present method allows a sequence determination to occur at sensitivities provided by a 13-mer (or higher base number) probe, but without the concomitant requirement for a large number of cells in a gel matrix pattern. For example, if in a first step, an unknown target strand of DNA or RNA is hybridized on an oligomer chip and two identical octamers are found on the strand, a need exists to determine the flanking regions surrounding those oligomers. In this scenario, the region containing the target strand duplexed with one of the octamers can be exposed to a pool of labeled pentamers in an effort to extend the octamer sequence to a 13-mer, an 18-mer or longer. The appropriate complementary pentamers, once identified via stacking hybridization, are then ligated onto the original immobilized probe (after the original immobilized probe is phosphorylated) to form a longer probe. The existence of this new, extended probe provides the sensitivity of a gel matrix containing all variants of the now-formed, longer oligonucleotide.

After construction of this longer probe, contiguous stacking hybridization then can be used in conjunction therewith to reconstruct larger fragment sequences of the target molecule.

EXAMPLE 4

Sequencing Unknown ssDNA Using Phosphorylation-Ligation Technique

FIG. 8 illustrates the utility of the probe-extending technique to determine the base sequence of an unknown target oligonucleotide strand. An exemplary 75-base fragment containing two sequences, each repeated once, was sequenced using the method. The 75-base fragment is designated as number 810 in FIG. 8. The two different sequences 812 and 814 are in bold and underlined, respectively.

The 75-base fragment 810 is subjected to a hybridization chip (not shown) containing all possible octamers. As a result of the hybridization step, a list, 816, of all heptamers (7-mers), with portions of immediately adjacent oligos, in the original 75-base fragment is generated. As can be noted, the sequence designated as "1." in the list 816 corresponds to the first seven bases of the 75-base fragment. The sequence designated as "2." in the list corresponds to the seven bases in the 75-base fragment starting with the second base thymine. Correspondingly, the sequence designated as "3." in the list corresponds to the seven bases in the 75-base fragment starting with the third base adenine. That the hybridization list, 816, contains only 46 unique heptamers indicates that some subfragments dwelling in the 75-base fragment are repeated.

Using the heptamer list 816 discussed above, seven subfragments having definitive base sequences are determined to exist in the 75-base fragment. A list, 818, of the seven subfragments, (i.e. subfragment numbers 1–7) further indicate (in the "frequency" column) the number of times each fragment appears in the 75-base fragment. Also determined from the subfragment analysis is which subfragments appear before and after a particular subfragment. A pictorial of this subfragment list and the relative positioning of subfragments viz. one another are depicted in 820 of FIG. 8.

The "before", "after", and "frequency" information of the subfragment list is then utilized to construct two possible 75-base sequences, 822 and 824, the first sequence 822 of which is the correct sequence. Also accompanying the two possible sequences, are the fragment positions. As can be observed, simply employing contiguous stacking hybridization using two pentamers with an immobilized octamer to produce an 18-mer hybrid will not result in differentiating between the original 75-base sequence 822 and the other 75-base possibility 824. As such, the octamer first must be phosphorylated and then ligated with two pentamers to produce an 18-mer probe, to which contiguous stacking hybridization can be applied to definitively determine the correct sequence.

In summary, the aforementioned method of phosphorylating and ligating oligos to form a foundation for later CSH is a powerful method for definitively sequencing long DNA or RNA molecules or similar structures.

While the invention has been described with reference to details of the illustrated embodiment, these details are not intended to limit the scope of the invention as defined in the appended claims.

The embodiment of the invention inwhich an exclusive property of privilege is claimed is defined as follows:

1. A method for detecting disease associated alleles in patient genetic material comprising:
   a) immobilizing a first group of oligonucleotide molecules having a known length on a predetermined position on a substrate, said oligonucleotide molecules synthesized to complement base sequences of the disease associated alleles;
   b) contacting the patient genetic material with said first group of oligonucleotides to form duplexes;
   c) contacting the duplexes with a second group of oligonucleotide molecules, said second group of oligonucleotide molecules to noncovalently to extend the length of the oligonucleotide molecules of the first group, and where each of the oligonucleotage molecules of the second group varies from each other in just one base position and where each of the oligonucleotide molecules of the second group are each tagged with a fluorochrome which radiates light at a predetermined wavelength; and
   d) comparing the light patterns radiating from the predetermined positions on the substrate with predetermined light patterns emitted from identical substrates which were contacted with the disease associated alleles.

2. The method as recited in claim 1 wherein the patient genetic material are polynucleotides selected from the group consisting of deoxyribonucleic acid and ribonucleic acid.

3. The method as recited in claim 1 wherein the oligonucleotide molecules of the first group of oligonucleotides and the oligonucleotide molecules of the second group of oligonucleotides contain a base selected from the group consisting of guanine, cytosine, adenine, thymine, uracil, and combinations thereof.

4. The method as recited in claim 1 wherein the oligonucleotide molecules of the first group of oligonucleotides consists of different oligonucleotide sequences and are of equal length.

5. The method as recited in claim 1 wherein the length of the oligonucleotides in the first group is between 8 and 20 bases.

6. The method as recited in claim 1 wherein the oligonucleotide molecules of the second group of oligonucleotides consist of different base sequences and are of equal length.

7. The method as recited in claim 1 wherein the predetermined length of the oligonucleotides in the second group is between 4 and 7 bases.

8. The method as recited in claim 1 wherein the fluorochrome which radiates light at a predetermined wavelength is selected from the group consisting of tetramethylrodamine, fluoresceine, Texas Red, Cascade Blue, rhodamine, HEX and combinations thereof.

9. The method as recited in claim 6 wherein the oligonucleotide molecules of the second group comprised of different base sequences are tagged with the same fluorochrome.

10. The method as recited in claim 6 wherein the oligonucleotide molecules of the second group comprised of different base sequences are tagged with different fluorochromes.

11. The method as recited in claim 1 wherein the substrate is a gel support.

12. The method as recited in claim 1 wherein the oligonucleotides in the first group and the oligonucleotides in the second group are further comprised of a universal base.

13. The method as recited in claim 12 wherein the universal base is selected from the group consisting of 5-nitroindole, 3-nitropyrrole, inosine, or a combination thereof.

14. The method as recited in claim 1 wherein the oligonucleotides of the second group are comprised of a universal base selected from the group consisting of 5-nitroindole, 3-nitropyrrole, inosine or a combination thereof.

* * * * *